US009879271B2

(12) United States Patent
Rakotondrafara et al.

(10) Patent No.: US 9,879,271 B2
(45) Date of Patent: Jan. 30, 2018

(54) IRES ELEMENTS FOR EXPRESSION OF POLYPEPTIDES AND METHODS OF USING THE SAME

(71) Applicant: Wisconsin Alumni Research Foundation, Madison, WI (US)

(72) Inventors: Aurelie Mamisoa Rakotondrafara, Madison, WI (US); Jincan Zhang, Jining shi (CN)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/593,700

(22) Filed: Jan. 9, 2015

(65) Prior Publication Data

US 2016/0040177 A1 Feb. 11, 2016

Related U.S. Application Data

(60) Provisional application No. 61/925,547, filed on Jan. 9, 2014.

(51) Int. Cl.
 *C12N 15/82* (2006.01)
 *C12N 15/113* (2010.01)
 *C12N 15/67* (2006.01)

(52) U.S. Cl.
 CPC ........ *C12N 15/8216* (2013.01); *C12N 15/113* (2013.01); *C12N 15/67* (2013.01); *C12N 15/82* (2013.01)

(58) Field of Classification Search
 None
 See application file for complete search history.

(56) References Cited

U.S. PATENT DOCUMENTS

| 5,933,378 A | 8/1999 | Gans et al. |
| 7,588,885 B2 | 9/2009 | Wu et al. |
| 8,809,017 B2 | 8/2014 | Yang et al. |
| 2006/0263882 A1 | 11/2006 | Fazio et al. |
| 2008/0057581 A1* | 3/2008 | Matsui ............... C12N 15/8216 435/419 |

OTHER PUBLICATIONS

Tatineni et al Triticum mosaic virus: a distinct member of the family potyviridae with an unusually long leader sequence. (2009) Virology; vol. 99; pp. 943-950.*
Tatineni et al. Triticum mosaic virus, complete genome. (2009) GenBank Accession FJ669487.1; pp. 1-5.*
Fellers, J.P. et al., "The complete genome sequence of Triticum mosaic virus, a new wheat-infecting virus of the High Plains," (2009) Arch Virol. 154(9):1511-1515 (Abstract).
Ha, S.-H. et al., "Application of two bicistronic systems involving 2A and IRES sequences to the biosynthesis of carotenoids in rice endosperm," (2010) Plant Biotechnology Journal 8:928-938.
Miller, W. A. et al., "Roles of cis-acting elements in translation of Viral RNAs," (2010) Plant Viruses: Molecular Biology. Horizon Press. In press.
Tatineni, S. et al., "Triticum mosaic virus: A distinct member of the family *Potyviridae* with an unusually long leader sequence," (2009) Virology 99(8):943-950.
Thompson, S. R., "Tricks an IRES uses to enslave ribosomes," (2012) Trends in Microbiology 20(11):558-566.
International Search Report and Written Opinion for International Application No. PCT/US2015/010772 dated Jun. 1, 2015 (16 pages).

* cited by examiner

*Primary Examiner* — Cathy Kingdon Worley
(74) *Attorney, Agent, or Firm* — Andrus Intellectual Property Law, LLP

(57) ABSTRACT

Compositions and methods for the expression of one or more coding sequences are provided which use an internal ribosome entry site (IRES) from *Triticum* mosaic virus (TriMV) to facilitate translation and expression of a polypeptide from an mRNA strand.

15 Claims, 13 Drawing Sheets

Figure 1
Fig. 1A
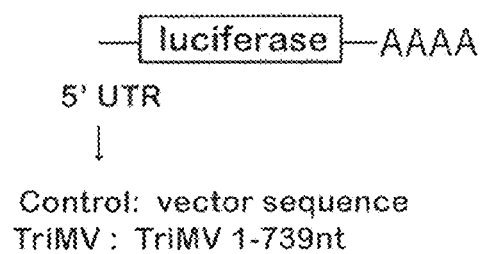
Control: vector sequence
TriMV : TriMV 1-739nt
Fig. 1B
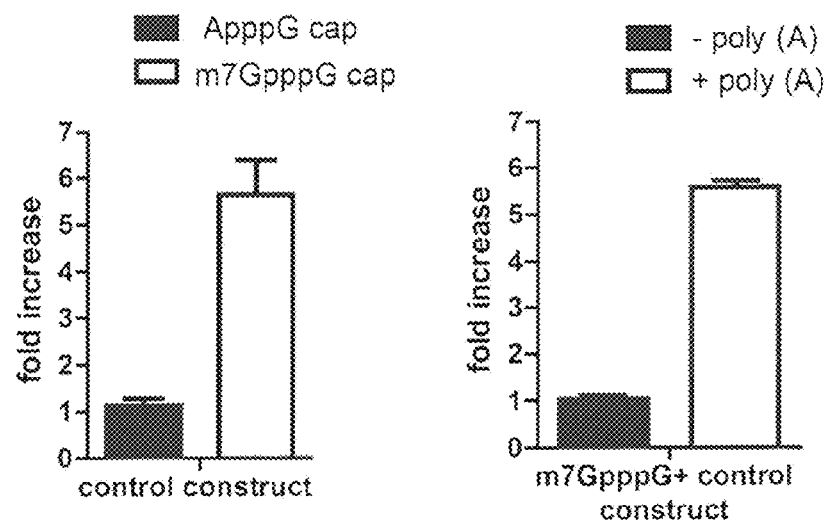

Figure 1 (Cont.)
Fig. 1C
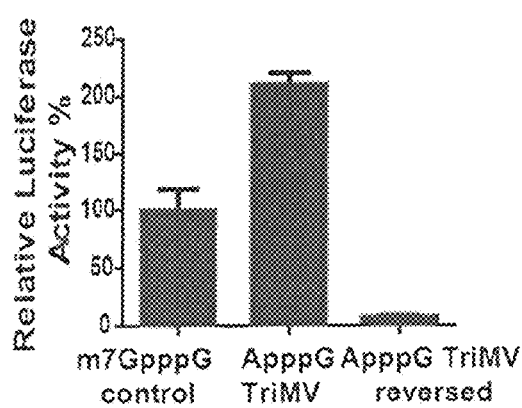
Fig. 1E
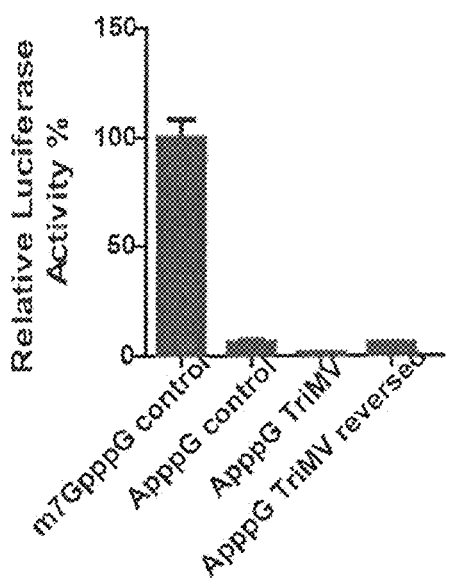
Fig. 1D
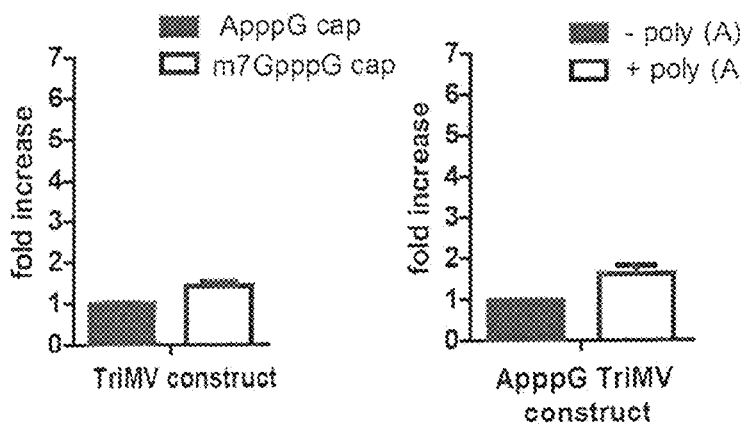

Figure 2
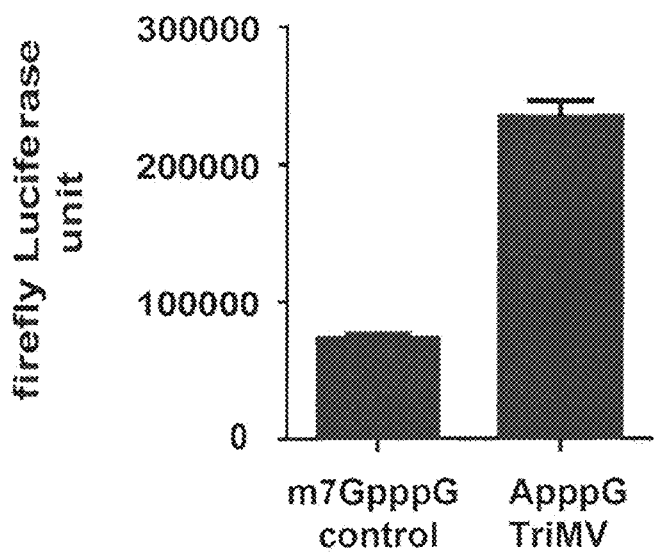
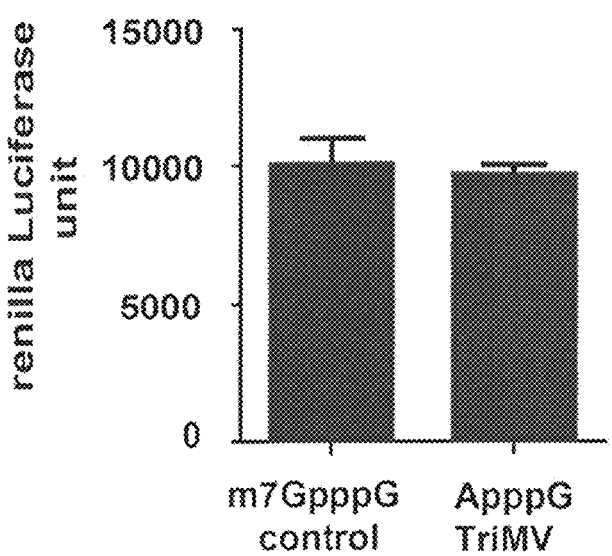

Figure 3
Fig. 3A
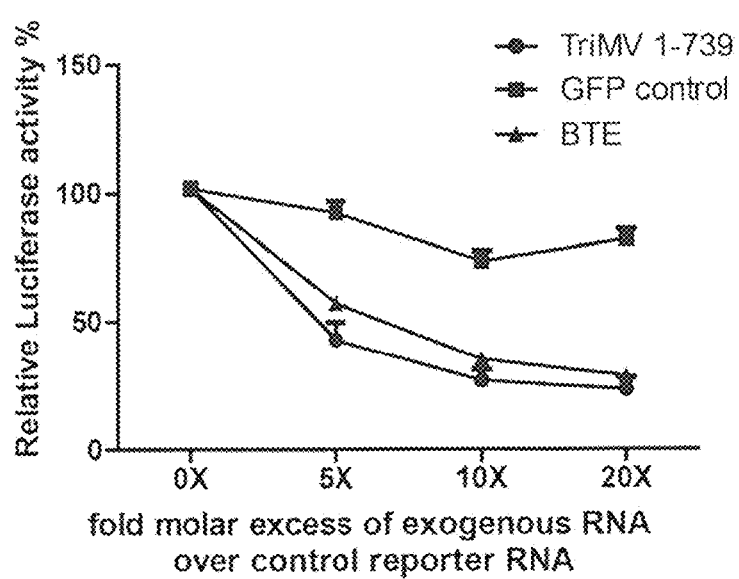
Fig. 3B
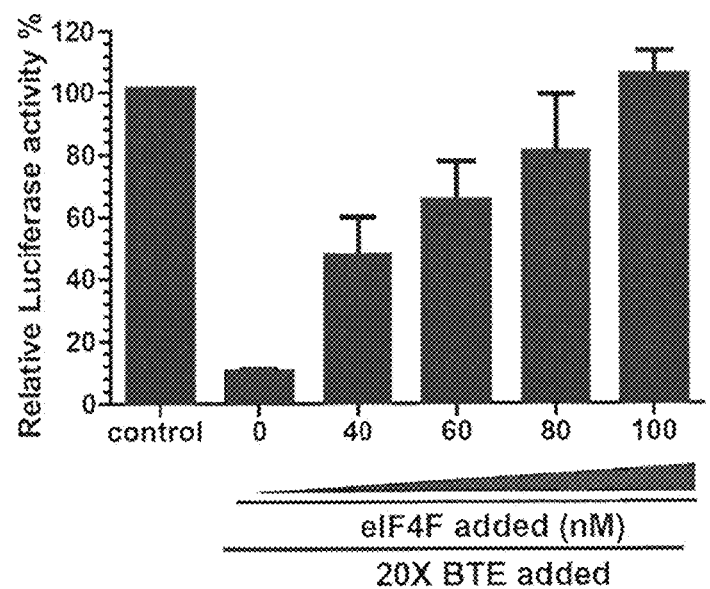

Figure 3 (Cont.)
Fig. 3C
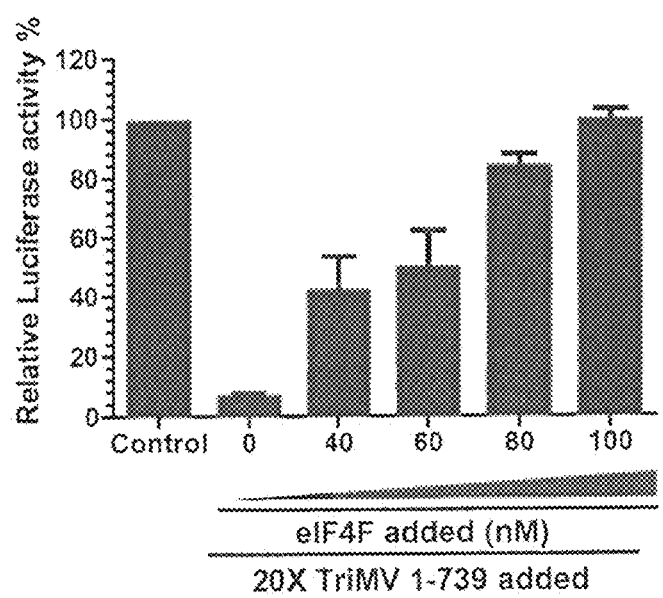
Fig. 3D
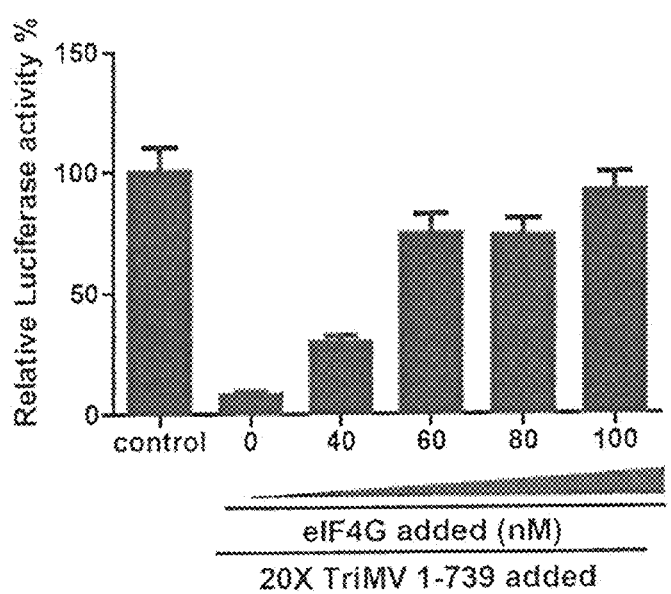

Figure 3 (Cont.)
Fig. 3E
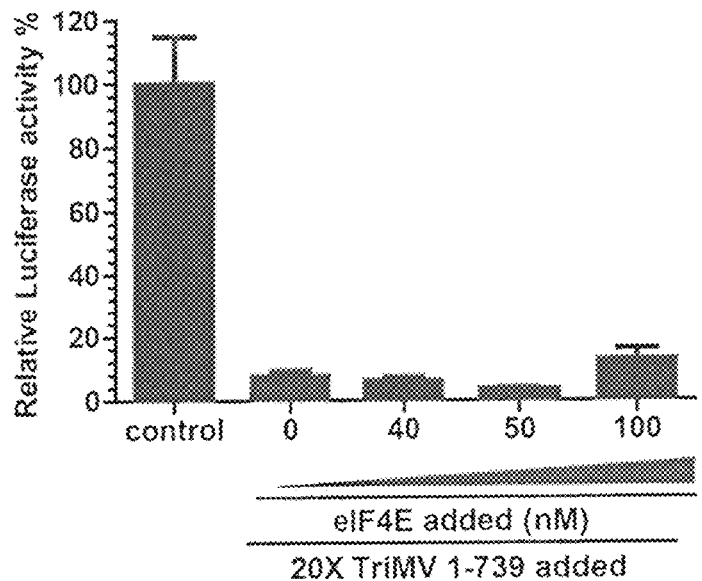
Figure 4
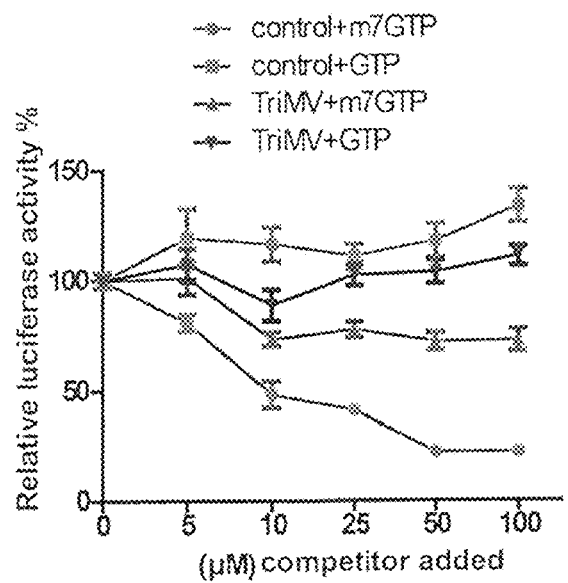

Figure 7
Fig. 7A
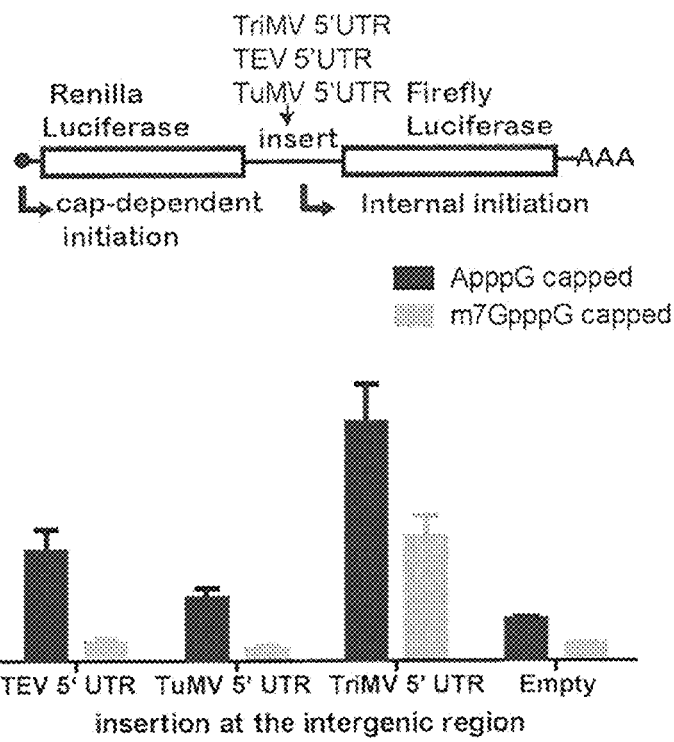
Fig. 7B
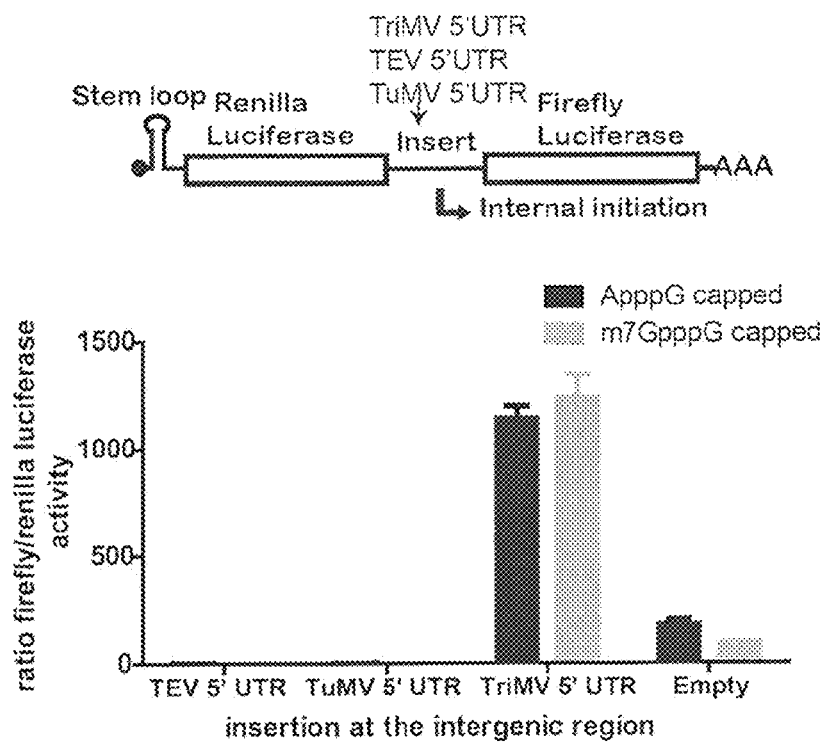

Figure 8
Fig. 8A
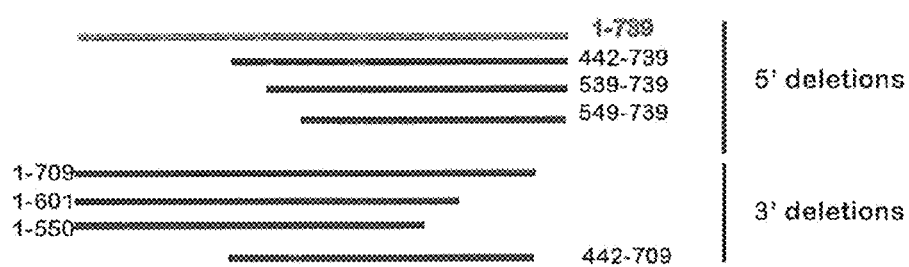
Fig. 8B
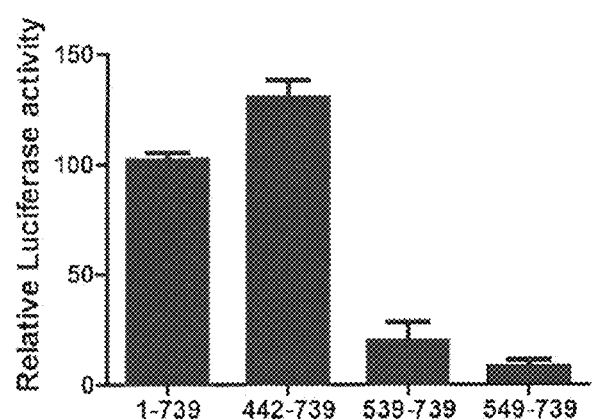
Fig. 8C
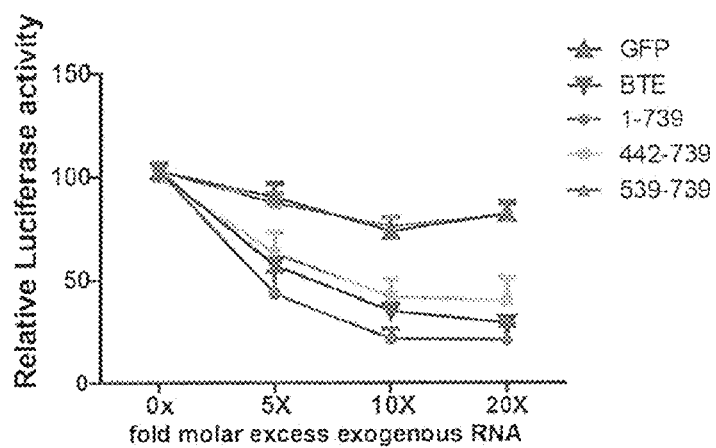

Figure 8 (Cont.)
Fig. 8D
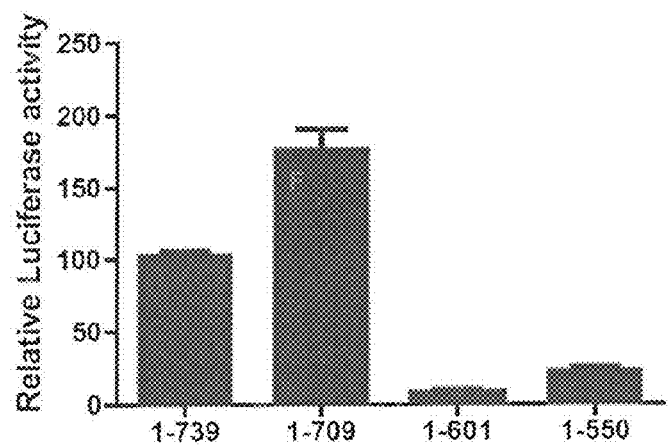
Fig. 8E
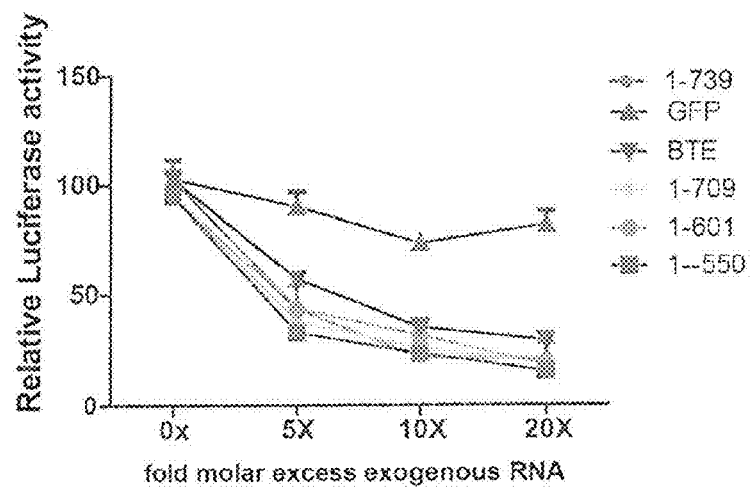

Figure 8 (Cont.)
Fig. 8F
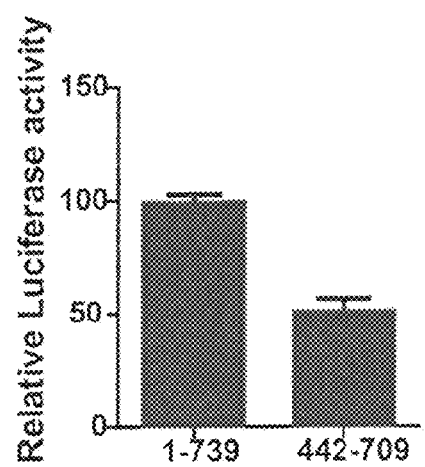
Fig. 8G
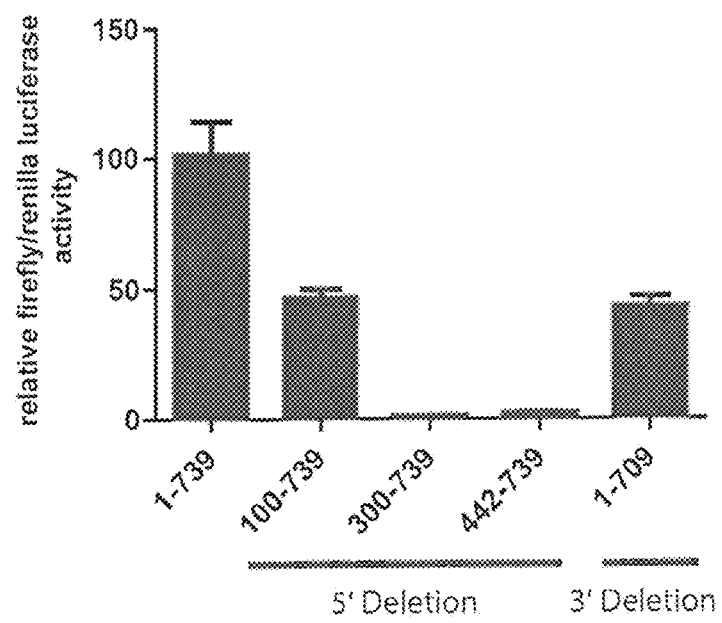

Figure 9

```
  1    aaaattaaag atcatattac ataaaataac ataatataaa atcacttaaa atcatgtgtt
 61    ttaaactacg cttagtttaa ttagttttgg tgcgtttagc gattcgtcat tgtacatggt
121    gtgttgtgtg ttttatgatt ttagtatgtt tcttaaatta ttgaagccct ataaggaccg
181    gctataaacg tcctgttttc aagtgggaaa agaaaccact cgccttacca ctagctggga
241    tctagctaga gctccggcgt aaaacgagct acgcttttgg atgcagcgtt acgcattcct
301    gggcttaggc gattgtacta caatgggtag cccccagtgc cagttttttgg cccgctattg
361    tattacaatt cggttaagtt aacttggttg gaaacaagcc aaatgctagc tatcattcgc
421    attcggacat gaggaaggtg aacgcagtga atcatagtgg tggtacgctc ttggggtggt
481    tcccaagact tcgtagggct atggttagct gttagtaaga cctaatgttc gtttgtgata
541    cagtcgaaag ttgtttccgt atggagctcg gtctgcgcgt taagcaccag cctgactatg
601    ggcagtatcc ctgtttttcc actattctca ctatcaacca caacgcacga ctttctgctc
661    tcttggcact ttcttacttt cacactctcg cgctcgtttc aaagtttttat tacttctctt
721    tttctcctga ccattcacga tg
```

(SEQ ID NO: 1)

IRES ELEMENTS FOR EXPRESSION OF POLYPEPTIDES AND METHODS OF USING THE SAME

CROSS-REFERENCE TO RELATED APPLICATIONS

This patent application claims the benefit of priority of U.S. Provisional Patent Application No. 61/925,547, filed Jan. 9, 2014, which is incorporated herein by reference in its entirety.

STATEMENT REGARDING FEDERALLY SPONSORED RESEARCH OR DEVELOPMENT

This invention was made with government support under 14-CRHF-0-6055 awarded by the USDA/NIFA. The government has certain rights in the invention.

SEQUENCE LISTING

This application is being filed electronically via EFS-Web and includes an electronically submitted Sequence Listing in .txt format. The .txt file contains a sequence listing entitled "2015-01-09_5671-00059_Sequence_Listing.txt" created on Jan. 7, 2015 and is 1,617 bytes in size. The Sequence Listing contained in this .txt file is part of the specification and is hereby incorporated by reference herein in its entirety.

BACKGROUND

Viral mechanisms of protein synthesis can be different from the canonical cellular protein synthesis. Many positive strand RNA viruses, which include animal and plant viruses within the Picornavirus-like super-family, do not have their RNA capped and yet they translate efficiently. In the absence of a 5' cap, a common strategy for the recruitment of ribosomes is via an internal ribosome entry site (IRES). An IRES is an RNA domain upstream of an open reading frame, which recruits the ribosomes internally onto the RNA independently of a 5' cap structure or ribosomal scanning from the 5' end. One main feature of an IRES is that when the IRES is placed in the intergenic region of a bicistronic mRNA, the element is capable of mediating translation of the downstream cistron, through internal recruitment of the translation machinery just upstream of the open reading frame. Translation of the downstream cistron is independent of the translation of the first (upstream) cistron. In a true IRES, translation of the downstream cistron is not effected by inclusion of an upstream stem loop structure located at or near the 5' end of the RNA, which is capable of inhibiting ribosome 5' end entry.

Based on their structural conformation and factor requirement, three groups of distinctive animal virus IRES elements have been defined. Class I IRES elements are found in the Dicistroviridae family, are compact in structure and are able to initiate translation alone from a non-AUG codon, without any host factors. Class II IRES elements are modeled by Hepatitis C virus. These IRES elements can recruit the 40S ribosome complex alone but they need factors like eIF3 and eIF2/GTP/Met-tRNAi complex to actually finish the initiation. Class III IRES elements are modeled by Encephalomyocarditis virus (EMCV) and Poliovirus. This type of IRES needs the helicase eIF4A, C-terminal region of eIF4G and often some cellular RNA binding proteins referred to as IRES-transacting factors (ITAF) to initiate translation.

All reported plant IRESes are short relative to those observed in animal viruses, have AU-rich sequences and are devoid of stable structure. IRESes in plant viruses are yet to be explored on a large scale. Tobacco etch virus (TEV), a member of the Potyviridae family, the largest group of plant viruses, has been the model system to study IRES-mediated translation in plants. The TEV reported IRES has two pseudoknot-containing domains at its 144 nucleotide 5' untranslated region needed to promote cap-independent translation. Potato virus Y, a serious disease for potato production worldwide, has a reported 55 nucleotide IRES in its 188 nucleotide 5' UTR. Plum pox virus, by contrast, has no specific sequence found to be required for its reported IRES function, with upstream AUG and leaky scanning possibly involved in its translation initiation.

Other IRES elements which have been reported within other plant virus families include Tobacco mosaic virus, a prototype of Tobamoviruses, which uses a 75 nucleotide IRES for the expression of its movement protein from the subgenomic RNA. Crucifer-infecting tobamovirus (crTMV) has an IRES located within an intergenic region for the translation of its coat protein. Potato leafroll virus (PLRV), the type species of the genus Polerovirus in the family Luteoviridae, directs internal ribosome entry with a GA rich motif (Jaag at al., 2003, *Proc Natl Acad Sci USA*, 100, 8939-8944).

However, the IRES activities of most reported plant viruses remain questionable as well as the degree and/or the context in which they sustain efficient translation. The methodology and experimental approaches used to identify the reported plant IRES elements do not allow an unambiguous conclusion of IRES activity. None of the reported plant IRES elements has been shown to sustain strong translation in the presence of an upstream stem loop structure blocking 5' end ribosome entry.

SUMMARY

A plant IRES and methods of using the IRES are provided herein and the full-length IRES is provided as SEQ ID NO: 1. The plant IRES is derived from a plant virus as described more fully herein. This IRES can mediate cap-independent translation of a coding sequence, translation of the second cistron of a bicistronic message and translation of a coding sequence when positioned downstream of a stable hairpin or stem-loop structure. The Examples also demonstrate that the full-length IRES of SEQ ID NO: 1 is not required for each of these activities.

In one aspect, a construct comprising at least nucleotides 442-709 of SEQ ID NO: 1 or a variant thereof upstream of a first heterologous coding sequence is provided. The construct may be a DNA construct that can be transcribed and translated in a cap-independent manner using the IRES of SEQ ID NO: 1 to initiate translation. Alternatively, the construct may be an RNA construct capable of being translated in a cap-independent manner in a cell-free translation assay.

In another aspect, a construct for expressing at least two polypeptides in a cell is provided. The construct includes a promoter operably linked to a first coding sequence encoding a first polypeptide, a DNA segment comprising at least nucleotides 442-709 of SEQ ID NO: 1 or a variant thereof downstream of the first coding sequence, and a second coding sequence encoding a second polypeptide operably linked to the DNA segment of SEQ ID NO: 1, such that upon introduction into the cell, the first coding sequence, the DNA segment of SEQ ID NO: 1 and the second coding sequence are transcribed as a single strand. Suitably, both the first and the second polypeptide are expressed after translation. Vectors, expression cassettes, cells, in particular plant cells, and transgenic plants comprising the constructs described herein are also provided.

In another aspect, a method for expressing at least two polypeptides in a cell includes the step of introducing into the cell a construct or a vector comprising the construct which includes a promoter operably linked to a first coding sequence encoding a first polypeptide, a DNA segment comprising at least nucleotides 442-709 of SEQ ID NO: 1 or variant thereof downstream of the first coding sequence, and a second coding sequence encoding a second polypeptide operably linked to the DNA segment of SEQ ID NO: 1, such that after introduction into the cell, the first coding sequence, the DNA segment of SEQ ID NO: 1 and the second coding sequence are transcribed as a single strand. Suitably the DNA segment of SEQ ID NO: 1 is sufficient to direct translation of the second coding sequence.

In an aspect, a method for expressing a polypeptide in a cell includes the step of introducing into the cell a polynucleotide comprising a promoter operably linked to a first coding sequence encoding the first polypeptide, and a segment comprising nucleotides 442-709 of SEQ ID NO: 1 or a variant thereof between the promoter and the coding sequence on the polynucleotide and expressing the first polypeptide in the cell by allowing for transcription of the segment of SEQ ID NO: 1 and the first coding sequence as a single strand and the segment of SEQ ID NO: 1 directs translation of the first coding sequence.

In yet another aspect, a method for expressing a polypeptide in a cell-free translation system includes the step of contacting a polynucleotide with a cell-free translation system to allow translation and expression of the polypeptide. The polynucleotide comprises nucleotides 442-709 of SEQ ID NO: 1 or variant thereof operably linked to a coding sequence encoding the polypeptide. The nucleotides of SEQ ID NO: 1 direct translation of the coding sequence. The translation is cap-independent and proceeds in the presence of a stable hairpin structure upstream of the nucleotides of SEQ ID NO: 1.

In a further aspect, a method for expressing at least two polypeptides in a cell-free system includes the step of contacting a polynucleotide with a cell free translation system. The polynucleotide comprises a first coding sequence encoding a first polypeptide, nucleotides 100-709 of SEQ ID NO: 1 or variant thereof downstream of the first coding sequence, and a second coding sequence encoding a second polypeptide operably linked the nucleotides of SEQ ID NO: 1. The nucleotides of SEQ ID NO: 1 are sufficient to direct translation of the second coding sequence.

Other aspects and embodiments of the disclosure will become apparent to one of skill in the art in light of the following description.

BRIEF DESCRIPTION OF THE DRAWINGS

FIG. 1 is a set of figures showing the role of the TriMV 5' leader in cap-independent translation. FIG. 1A shows a schematic of the monocistronic luciferase reporter constructs. The luciferase gene is flanked at its 5' end either with the TriMV viral 5' leader (1-739) (TriMV construct: SEQ ID NO: 1) or with an m7GpppG capped 140 nt vector sequence (control construct) and with a 62 nt long poly (A) tail at its 3' end. FIG. 1B is a set of graphs showing the relative luciferase activity (fold increase) in wheat germ extract of the TriMV (SEQ ID NO: 1) and the m7GpppG capped vector sequence mRNA constructs and the poly (A) tail dependence of translation. Luciferase measurements were standardized by the mean of the luciferase measurements of the control RNA. FIG. 1C is a graph showing the relative luciferase activity in wheat germ extracts of the mRNA constructs containing the TriMV leader (SEQ ID NO: 1) as compared to the vector sequence as 5' UTR with the presence of a 5' m7GpppG cap or the TriMV 5' leader sequence reversed and an ApppG cap analog. The ApppG cap analog has no function in translation. FIG. 1D is a set of graphs showing the fold increase of luciferase activity in wheat germ extract of the TriMV mRNA (SEQ ID NO: 1) reporter constructs with and without a m7GpppG cap and in the presence or the absence of a 3' poly (A) tail. FIG. 1E is a graph showing the relative luciferase activity of the TriMV mRNA (SEQ ID NO 1) reporter construct as compared to m7GpppG cap or ApppG cap analog control sequence in rabbit reticulocyte lysate.

FIG. 2 is a set of graphs showing that the TriMV 5' UTR (SEQ ID NO: 1) drives efficient cap-independent translation in vivo in oat protoplasts.

FIG. 3 is a set of figures showing the results of the trans-inhibition assay of free TriMV 5'UTR RNA (SEQ ID NO: 1) against the capped and polyadenylated vector reporter in wheat germ extract. FIG. 3A is a graph showing the results of the trans-inhibition assay with increasing molar excess of competing free RNA against the capped and polyadenylated vector reporter in wheat germ extract. A concentration of 0 to up to 20 fold molar excess of the competing free RNA corresponding to the TriMV leader (TriMV 1-739: SEQ ID NO: 1), the Barley yellow dwarf virus translation enhancement element (BTE) or a 700 nt RNA sequence of the green fluorescent protein (GFP) coding region were added to the translation reaction. FIG. 3B is a graph showing the restoration of the cap-dependent translation by increasing concentrations of eIF4F in wheat germ inhibited by addition of 20 fold molar excess of BTE. FIG. 3C is a graph showing restoration of the cap-dependent translation by increasing concentrations of eIF4F in wheat germ inhibited by addition of 20 fold molar excess of TriMV. FIG. 3D is a graph showing restoration of the cap-dependent translation by increasing concentrations of eIF4G in wheat germ inhibited by addition of 20 fold molar excess of TriMV. FIG. 3E is a graph showing the lack of restoration of the cap-dependent translation by increasing concentrations of eIF4E in wheat germ inhibited by addition of 20 fold molar excess of TriMV.

FIG. 4 is a graph showing the relative luciferase activity in wheat germ extract of the TriMV 5' UTR (SEQ ID NO: 1) and control mRNA constructs in the presence of an increasing concentration of GTP or m7GTP cap analog.

FIG. 7 is a set of figures showing the IRES activity of the TriMV 5' leader (SEQID NO: 1). FIG. 7A is a schematic of the standard bicistronic dual luciferase reporter construct and the position of insertion of the RNA elements to be tested. While the translation of the renilla luciferase gene is cap-mediated, the translation of the downstream firefly luciferase gene can only be mediated by internal initiation driven by the RNA sequence inserted in the intergenic region. The IRES activity is defined by the ratio of the firefly luciferase activity over that of the renilla luciferase. FIG. 7A also provides a graph showing the IRES activity in wheat germ extract of bicistronic mRNA constructs containing the TriMV 5' UTR, Tobacco etch virus (TEV) 5' UTR, Turnip mosaic virus (TuMV) 5' UTR or no insertion control (empty). FIG. 7B is a schematic of the bicistronic luciferase reporter construct with a stable hairpin insertion right at the 5' end of the mRNA. FIG. 7B also provides a graph showing the IRES activity in wheat germ extract of bicistronic mRNA constructs containing the TriMV 5' UTR, TEV IRES, TuMV IRES or no insert empty control, in the presence of the stable hairpin at the 5' end of the mRNA.

FIG. 8 is a set of figures to determine the minimal region within the TriMV 5' UTR (SEQ ID NO: 1) required for cap-independent translation in a monocistronic mRNA. FIG. 8A is a schematic of the 5' and 3' deletions to TriMV 5' leader tested in the assays. FIG. 8B is a graph showing the relative luciferase activity of 5' deletion mutants compared to the full length 5' UTR. Luciferase light measurements are standardized by full length TriMV 5' UTR luciferase light measurements. FIG. 8C is a graph showing the in vitro trans-inhibition assay of cap-dependent translation with a fold molar excess of the 5' deletion RNA mutants. FIG. 8D is a graph showing the relative luciferase activity of 3' deletion mutants compared to that of full length 5' UTR. Luciferase light measurements are standardized by full length TriMV 5' UTR luciferase light measurements. FIG. 8E is a graph showing the in vitro trans-inhibition assay of cap-dependent translation with fold molar excess of the 3' deletion RNA mutants. FIG. 8F is a graph showing the relative luciferase activity of the deletion mutant 442-709 compared to that of the full length TriMV 5' UTR. Luciferase light unit measurements are standardized by full length TriMV 5' UTR luciferase light unit measurements. FIG. 8G is a graph showing the relative IRES activity of TriMV deletion mutants in the bicistronic construct compared with that of entire 5' UTR. TriMV 5' UTR deletion mutants that were defined in the monocistronic constructs were also inserted into pDluc to test IRES activity. IRES activities were standardized to the full length TriMV 5' UTR.

FIG. 9 shows the 739 polynucleotide Triticum mosaic virus (TriMV) IRES 5' untranslated region (UTR) and presumed start codon (GenBank: FJ669487.1) (SEQ ID NO: 1). Upstream AUGs are bold and underlined, and the polypyrimidine tract is underlined. GC content: 42%.

DETAILED DESCRIPTION

Figure 5:
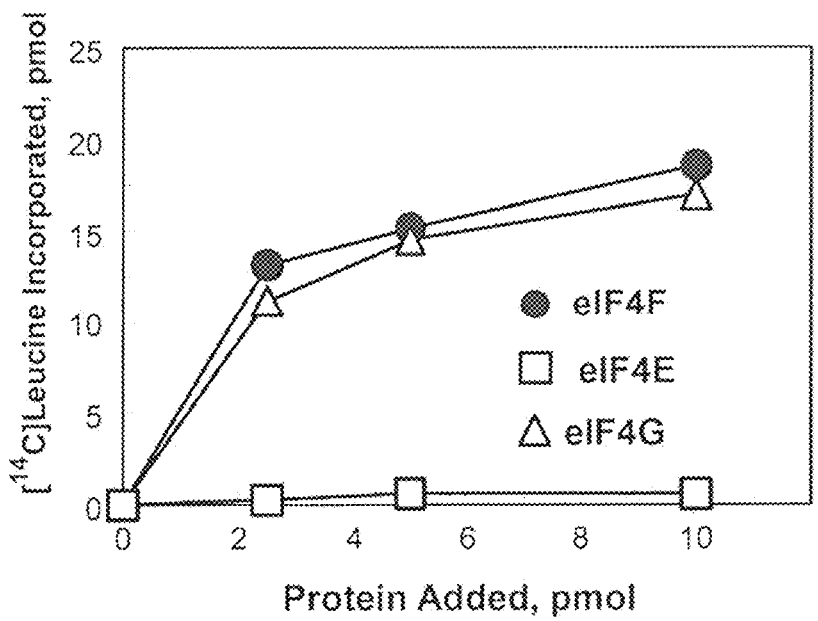
FIG. 5 is a graph showing that the TriMV 5' UTR (SEQ ID NO: 1) mediated translation is dependent on the addition of translation factors, but independent of eIF4E.

The present disclosure relates to plant internal ribosome entry site (IRES) sequences which can be used to direct translation of a polypeptide encoded internally in an mRNA sequence and/or in a cap independent manner. The IRES presented herein may also function as a translation enhancer for transcripts comprising a cap and poly-A tail. Compositions and methods for expression of one, two, or more polypeptides in a cell or expression system such as a cell-free expression system which includes the IRES described herein are provided. The IRES is transcribed in the same strand upstream of the coding sequence of interest and permits translation of the coding sequence by recruitment and attachment of a ribosome to the internal sequence of the transcribed mRNA independently of the 5' end.

SEQ ID NO: 1 comprises an IRES isolated from Triticum mosaic virus (TriMV). The TriMV IRES (SEQ ID NO: 1) is a 739 polynucleotide sequence and permits translation of RNA without a cap, and is capable of effecting expression of a downstream coding sequence from an internal position of the RNA even in the presence of a stable hairpin or stem loop structure upstream of the IRES and coding sequence. The IRES permits expression of two or more coding sequences from the same RNA strand. The first coding sequence may be optionally translated using the 5' cap structure and thus the typical ribosome attachment and translation mechanism from the 5' end of the mRNA. Expression of the first and/or subsequent coding sequence can be facilitated by internal recruitment and attachment of the ribosome to the mRNA by the one or more IRES sequences.

Complements and variants of SEQ ID NO: 1 are envisaged. A variant is a sequence sharing substantial identity with SEQ ID NO 1, but which is able to facilitate translation of a coding sequence by internal recruitment of a ribosome in a similar manner as SEQ ID NO: 1. A variant of nucleotides 1-739 of SEQ ID NO: 1 may facilitate the full spectrum of functionalities of the IRES or may have somewhat limited functionalities. As demonstrated in the Examples, truncation mutations of nucleotides 1-739 of SEQ ID NO: 1 may retain only some of the functions of the full length IRES. Some truncations were able to initiate cap-independent translation, but lacked other functions, such as the ability to initiate translation when placed at an internal position. Other truncations were able to increase translation of a coding sequence, but to a lesser extent than the full length IRES. Those of skill in the art will appreciate that these truncations described in the Examples or other similar truncations would retain enough function to be desirable in particular applications.

SEQ ID NO: 1 efficiently drives cap-independent translation both in vivo and in vitro. It is more efficient than prototype plant virus IRESes. In the Examples the IRES of SEQ ID NO: 1 was at least two fold more active than plant IRESes from Tobacco etch virus (TEV) and Turnip mosaic virus (TuMV). In addition, no other plant viruses identified to date have been shown to maintain strong translation initiation of a downstream coding sequence when positioned downstream of a stable hairpin structure. The IRES described herein does not require a cap and uses the 3' poly (A) tail for full translation activity in vitro. SEQ ID NO: 1 efficiently trans-inhibits cap-dependent translation, and this inhibition can be reversed by the addition of eIF4F complex (including eIF4G and eIF4E) and by eIF4G alone, but not eIF4E alone. The inhibition can also be reversed by eIFiso4F which is an isoform found only in plants.

The entire 739 nucleotide sequence of SEQ ID NO: 1 provides full IRES activity, but truncations as noted above also showed some functionality. In particular, nucleotides 442-739 and 1-709 were demonstrated to provide full translation or even to increase translation of the mRNA as compared to nucleotides 1-739 in the context of a monocistronic mRNA. Nucleotides 442-709 were shown to allow for translation initiation of the mRNA, but at reduced levels of translation as compared to the full-length IRES. Nucleotides 100-739 and 1-709 were also shown to allow for translation initiation of both monocitronic and bicistronic constructs, but at a reduced level as compared to 1-739. In contrast, nucleotides 300-739 and 442-739 were not capable of initiating translation in the bicistronic constructs. These results are demonstrated in the examples. Those of skill in the art will appreciate that these truncations may be useful in a scenario where the number of nucleotides in a construct must be limited due to size or efficiency constraints of the system in which the IRES is being used or the amount of translation required to produce a sufficient amount of the polypeptide for the application of interest.

The compositions include constructs, vectors, plasmids or expression cassettes which at least a portion of the plant IRES of SEQ ID NO: 1 described herein. Constructs include single-stranded RNA, double-stranded RNA, single-stranded DNA, double-stranded DNA segments or ambisense RNA. The constructs may comprise at least nucleotides 442-709 of SEQ ID NO: 1 or a variant thereof operably connected to a first heterologous coding sequence encoding a first polypeptide. Under appropriate conditions the construct mediates translation of the first heterologous coding sequence and production of the first polypeptide. In other embodiments, the constructs include a promoter operably linked to a first coding sequence encoding a first polypeptide, a segment comprising at least nucleotides 442-709 of SEQ ID NO: 1 or variant thereof downstream of the first coding sequence and a second coding sequence encoding a second polypeptide operably linked to the segment of SEQ ID NO: 1 or variant thereof. Suitably, the construct is capable of initiating translation of both the first polypeptide and the second polypeptide. The segment of SEQ ID NO: 1 may include only nucleotides 442-709 or may include only or at least nucleotides 442-739, 1-709, 100-709, 100-739 or 1-739 of SEQ ID NO: 1. The segment of SEQ ID NO: 1 including the IRES should be positioned just upstream of a start codon. For example in SEQ ID NO: 1, the IRES is found at nucleotides 1-739 and nucleotides 740-742 encode a start codon. Suitably, the start codon is positioned such that the coding sequence is in frame with the start codon.

The first coding sequence and/or the second coding sequence may be heterologous sequences, i.e., suitably the coding sequences are not natively associated with the IRES of SEQ ID NO: 1. The coding sequences may not be derived from TriMV. Suitably the coding sequences are plant derived sequences. Alternatively, the coding sequences are not plant derived. The coding sequences may be altered, e.g., mutated to allow for better expression such as through preferred codon usage to increase expression of the polypeptides encoded by the coding sequences.

The constructs may be used in cell-free translation systems or may be inserted in vectors or as portions of expression cassettes that can be inserted into the genome of cells. Vectors include monocistronic, bicistronic and multicistronic vectors for translation of one, two, three or more polypeptides. Vectors include, but are not limited to viral, plasmid, BAC, YAC or other vectors capable of carrying or moving RNA or DNA segments from one cell to another cell or existing in a cell-free state. The compositions include cell-free translation systems which can be used to express proteins in vitro. In vivo expression in cells, protoplasts, plants, fungi and bacteria is also envisaged. In vivo expression in protoplasts is demonstrated in the Examples. In vivo expression from extra-chromosomal vectors or after incorporation of the construct into the genome of the cell using methods available to those of skill in the art is also envisaged.

Cell-free translation systems are based on the cellular ribosomal protein synthesis system and are widely used by those of skill in the art. Generally, an RNA construct is added to a translation system that is composed of a cell extract (referred to as the S30 fraction) from *Saccharomyces cerevisiae*, wheat germ, rabbit reticulocytes, HeLa cells, *drosophila* S2 cells or other cell types. These extracts are known in the art and may be supernatants from a 30 000 g centrifugation. They contain components such as ribosomes, translation factors, aminoacyl-tRNA synthetases, and tRNAs, which are required for the production of polypeptides. Efficient polypeptide production may require supplementation of the S30 extract with magnesium and potassium salts, as well as several enzymes for energy regeneration and their substrates. The DNA constructs provided herein may also be used in in vitro cell free transcription and translation systems such as TNT from Promega Corp. The TriMV UTR has been shown to work efficiently to mediate translation in wheat germ extract, but did not mediate translation in rabbit reticulocyte lysate or HeLa cell extract in initial experiments. We believe the TriMV UTR may require a factor or condition not present in rabbit reticulocyte lysate or HeLa cell extracts or may require supplementation with a plant specific factor, such as a plant eIF4F.

In one embodiment, a wheat germ extract transcription and translation system is employed. For example, the barley yellow dwarf virus element permits expression of a first coding sequence without the requirement for a cap structure on the mRNA. Incorporation of the TriMV IRES downstream of the first coding sequence and upstream of a second coding sequence, for example, in a bicistronic RNA construct, facilitates expression of a second coding sequence. Subsequent polypeptides may be expressed from subsequent IRES elements.

Generally, the nomenclature used herein and the laboratory procedures utilized in the present invention include molecular, biochemical, microbiological and recombinant DNA techniques that are well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Such techniques are thoroughly explained in the literature and are generally performed according to Sambrook et al., 1989, Molecular Cloning—A Laboratory Manual, Cold Spring Harbor Laboratory, Cold Spring Harbor, New York, N.Y.; Ausubel et al., 1993, Current Protocols in Molecular Biology, Volumes 1-3, John Wiley & Sons, Inc., Hoboken, N.J.; and Kriegler, 1990, Gene Transfer and Expression: A Laboratory Manual, Stockton Press, New York, N.Y.; Perbal, 1988, A Practical Guide to Molecular Cloning, $2^{nd}$ edition, John Wiley & Sons, New York, N.Y.; Watson et al., 1992, Recombinant DNA, $2^{nd}$ edition, Freeman & Co., New York, N.Y.; Bartlett and Stirling, 2003, PCR Protocols, $2^{nd}$ edition, Humana Press, Totowa, N.J.; all of which are incorporated herein by reference.

The compositions and methods described herein include monocistronic, bicistronic or multicistronic constructs and vectors that may be linear or circular, and permit expression of one, two, three or more polypeptides without needing a 5' mRNA cap structure. The first, second and third or more polypeptides are translated and expressed from the same strand of RNA. The first polypeptide may be translated using an IRES or via the 5' cap, the second and subsequent polypeptides are translated from one or more IRES sequences which facilitate internal attachment of the ribosome to the RNA strand and cap-independent translation of the coding sequence. The IRES may result in the ability to translate a downstream coding sequence even in the presence of a stable hairpin structure upstream of the IRES. The presence of the IRES may allow for translation even under conditions that shut off cap-dependent translation, such as eIF4E depletion or in response to stress or other physiological stimuli in which cells are able to shut off general translation. RNAs that have an IRES, such as those described herein are able to maintain their translation under these conditions.

In the constructs provided in the Examples, the IRES sequence starts 40 nucleotides downstream of the stop codon of the first cistron. But there is no restriction per se on the distance between the end of the first coding sequence and the beginning of the segment comprising the IRES. Suitably, the spacer between the end of the upstream coding sequence and the segment comprising the IRES is at least 10, 20, 30, 40, 50, 60, 70, 80, 90 or 100 nucleotides. The most important aspect from a translational point of view is that the TriMV RNA IRES is property folded (as often structure/folding is tightly linked to function) and including a spacer is always ideal if space in the construct allows. Suitably the downstream coding sequence whose translation is initiated via the IRES is arranged such that the cistron is in frame with the correct AUG initiation codon of the TriMV IRES sequence. TriMV has several upstream AUGs, as identified in FIG. 9, but these are believed to not be used as initiation sites. The start codon at nucleotides 740-742 is included in the constructs used herein and was shown to be the start codon used for translation initiation in the Examples. In an aspect, a first coding sequence is provided upstream of the IRES which first coding sequence is preceded by a stable hairpin structure to prevent or moderate translation of the first coding sequence. A second coding sequence is provided downstream of the IRES.

The phrase "nucleic acid" or "polynucleotide sequence" refers to a single-stranded or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

A "coding sequence" or "coding region" refers to a nucleic acid molecule having sequence information necessary to produce a gene product, when the sequence is expressed. The phrase "nucleic acid sequence encoding" refers to a nucleic acid which directs the expression of a specific protein or polypeptide. The nucleic acid sequences of this invention include both the DNA strand sequence that is transcribed into RNA and the RNA sequence that is translated into protein. The nucleic acid sequences include both the full length nucleic acid sequences as well as non-full length sequences derived from the full length sequences. It should be understood that the sequences include the degenerate codons of the native sequence or sequences which may be introduced to provide codon preference in a specific host cell.

The terms "isolated," "purified," or "biologically pure" refer to material that is substantially or essentially free from components that normally accompany it as found in its native state. Purity and homogeneity are typically determined using molecular biology and analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

An "expression cassette" refers to a nucleic acid construct, which when introduced into a host cell, results in transcription and/or translation of a RNA and/or polypeptide, respectively. The expression cassette may include a nucleic acid comprising a promoter sequence, with or without a sequence containing mRNA polyadenylation signals, and one or more restriction enzyme sites located downstream from the promoter allowing insertion of heterologous gene sequences. The expression cassette is capable of directing the expression of a heterologous protein when the gene encoding the heterologous protein is operably linked to the promoter by insertion into one of the restriction sites. The recombinant expression cassette allows expression of the heterologous protein in a host cell when the expression cassette containing the heterologous protein is introduced into the host cell. Expression cassettes can be derived from a variety of sources depending on the host cell to be used for expression. For example, an expression cassette can contain components derived from a viral, bacterial, insect, plant, or mammalian source. In the case of both expression of transgenes and inhibition of endogenous genes (e.g., by antisense, or sense suppression) the inserted polynucleotide sequence need not be identical and can be "substantially identical" to a sequence of the gene from which it was derived. Preferably the recombinant expression cassette allows expression at an early stage of infection and/or it allows expression in substantially all cells of an organism, such as a plant. Examples of expression cassettes suitable for transformation of plants can be found in U.S. Pat. Nos. 5,880,333 and 6,002,072; International Patent Publications Nos. WO/1990/002189 and WO/2000/026388; Ainley and Key, 1990, Plant Mol. Biol. 14: 949-967; and Birch, 1997, Annu. Rev. Plant Physiol. Plant Mol. Biol. 48: 297-326, all of which are herein incorporated by reference.

The term "host cell" refers to a cell from any organism. Preferred host cells are derived from plants, bacteria, yeast, fungi, insects, or other animals. The term "recombinant host cell" (or simply "host cell") refers to a cell into which a recombinant expression vector has been introduced. It should be understood that the term "host cell" is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Methods for introducing polynucleotide sequences into various types of host cells are well known in the art. Provided are host cells or progeny of host cells transformed with the recombinant expression cassettes of the present invention. The host cells may be plant cells.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression cassette. Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In certain embodiments, the coding sequence and IRES element are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

Promoters useful in the practice of the present invention include, but are not limited to, constitutive, inducible, temporally-regulated, developmentally regulated, chemically regulated, tissue-preferred and tissue-specific promoters. Suitable promoters for expression in plants include, without limitation, the 35S promoter of the cauliflower mosaic virus, ubiquitine, tCUP cryptic constitutive promoter, the Rsyn7 promoter, pathogen-inducible promoters, the maize In2-2 promoter, the tobacco PR-1a promoter, glucocorticoid-inducible promoters, oestrogen-inducible promoters and tetracycline-inducible and tetracycline-repressible promoters. Other promoters include the T3, T7 and SP6 promoter sequences, which are often used for in vitro transcription of RNA.

The term "nucleic acid construct" or "DNA construct" is sometimes used to refer to a coding sequence or sequences operably linked to appropriate regulatory sequences and inserted into an expression cassette for transforming a cell or for translating a protein in a cell-free system. Such a nucleic acid construct may contain a coding sequence for a gene product of interest, and optionally a selectable marker gene and/or a reporter gene. The term "selectable marker gene" refers to a gene encoding a product that, when expressed, confers a selectable phenotype, such as antibiotic resistance, on a transformed cell. The term "reporter gene" refers to a gene that encodes a product which is easily detectable by standard methods, either directly or indirectly. Reporter genes include, but are not limited to luciferases, β-glucuronidase (GUS), fluorescent proteins such as green fluorescent protein (GFP), dsRed, mcherry and others available to those skilled in the art, chloramphenicol acetyltransferase (CAT), and antibiotic resistant markers.

A "heterologous" region of a nucleic acid construct is an identifiable segment (or segments) of the nucleic acid molecule within a larger molecule that is not found in association with the larger molecule in nature. When the heterologous region encodes a plant gene, the gene will usually be flanked by DNA that does not flank the plant genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct" is also used to refer to a heterologous region, particularly one constructed for use in transformation of a cell.

The term "vector" is intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A "nucleic acid probe" or "oligonucleotide" is defined as a nucleic acid capable of binding to a target nucleic acid of complementary sequence through one or more types of chemical bonds, usually through complementary base pairing, usually through hydrogen bond formation. As used herein, a probe may include natural bases (i.e., A, G. C, or T) or modified bases (7-deazaguanosine, inosine, etc.). In addition, the bases in a probe may be joined by a linkage other than a phosphodiester bond, so long as it does not interfere with hybridization. For example, probes may be peptide nucleic acids (PNAs) in which the constituent bases are joined by peptide bonds rather than phosphodiester linkages. It will be understood that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence (sequence fragment).

A polynucleotide "exogenous to" or heterologous to an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, microinjection, in planta transformation techniques, and the like. These and similar methods are well-known and available to those skilled in the art.

Increased or enhanced expression of a polypeptide, or increased or enhanced expression of a polynucleotide encoding a polypeptide refers to an augmented change in expression of the polypeptide or protein. Examples of such increased expression includes increased expression of the sequence encoding the protein from the plant IRES element above the level of that resulting from translation using an alternate ribosome-binding translation system in a comparable expression system.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence. In the case of both expression of transgenes and inhibition of endogenous genes (e.g., by antisense or sense suppression) the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, because of codon degeneracy, a number of polynucleotide sequences will encode the same polypeptide. These variants are specifically covered by the term "polynucleotide sequence from" a particular polypeptide or a polynucleotide encoding a particular polypeptide sequence.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Optimal alignment of sequences for comparison may be conducted by methods commonly known in the art, for example by the search for similarity method described by Pearson and Lipman 1988, Proc. Natl. Acad. Sci. USA 85: 2444-2448, by computerized implementations of algorithms such as GAP, BESTFIT, BLAST, FASTA, and TFASTA in the Wisconsin Genetics Software Package, Genetics Computer Group (GCG), Madison, Wis., or by inspection. In a preferred embodiment, protein and nucleic acid sequence identities are evaluated using the Basic Local Alignment Search Tool ("BLAST"), which is well known in the art (Karlin and Altschul, 1990, Proc. Natl. Acad. Sci. USA 87: 2267-2268; Altschul et al., 1997, Nucl. Acids Res. 25: 3389-3402), the disclosures of which are incorporated by reference in their entireties. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990). The BLAST programs can be used with the default parameters or with modified parameters provided by the user.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least about: 25%. 30%, 35%, 40%, 45%, 50%, 55%, 60%, 65%, 70%. 75%, 80%, 85%, 86%, 87%, 88%, 89%, 90%, 91%, 92%, 93%, 94%, 95%, 96%, 97%, 98% or 99% sequence identity compared to a reference sequence.

The invention also relates to nucleic acids that selectively hybridize to the exemplified sequences, including hybridizing to the exact complements of these sequences. The specificity of single-stranded DNA to hybridize complementary fragments is determined by the "stringency" of the reaction conditions (Sambrook et al, 1989). Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer, or oligonucleotide to hybridize only to its target sequence (e.g., SEQ ID NO:1). Stringent conditions are sequence-dependent and will differ. Stringent conditions comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, e.g. 50% (v/v) formamide, 0.1% bovine serum albumin, 0.1% Ficoll, 0.1% polyvinylpyrrolldone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%. 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent, such that a polynucleotide will hybridize to the entire, fragments, derivatives, or analogs of the target sequence (e.g., SEQ ID NO:1). One example comprises hybridization in 6×SSC, 5×Denhardt's solution, 0.5% SDS and 100 µg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (Ausubel et al., 1993; Kriegler, 1990).

"Low stringent conditions" use washing solutions and hybridization conditions that are less stringent than those for moderate stringency, such that a polynucleotide will hybridize to the entire, fragments, derivatives, or analogs of the target sequence (e.g., SEQ ID NO:1). A nonlimiting example of low stringency hybridization conditions includes hybridization in 35% formamide. 5×SSC, 50 mM Tris HCl (pH 7.5), 5 mM EDTA, 0.02% PVP, 0.02% Ficoll, 0.2% BSA, 100 µg/ml denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (Ausubel et al., 1993; Kriegler, 1990).

Figure 10:
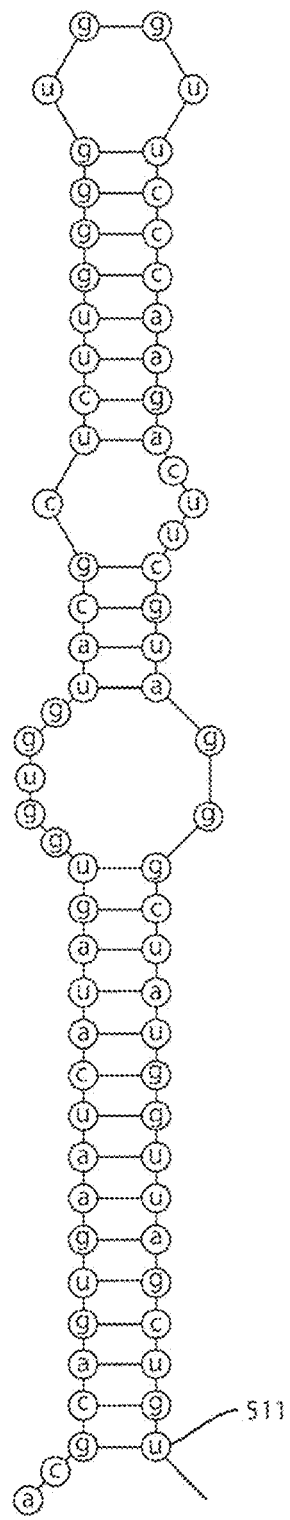
FIG. 10 is a schematic depiction of a structural prediction of a portion of the 5' leader sequence of the TriMV UTR (SEQ ID NO: 1) between nucleotides 441 and 511 made using the mFold program.

The plant IRES is at least 200, 225, 250, 275, 300, 325, 350, 375, 400, 425, 450, 475, 500, 525, 550, 575, 600, 625, 650, 675, 700, 725, 730, 735, or 739, nucleotides in length. Additional spacer sequence may be added either before or after the IRES and the IRES may precede a start codon. In certain embodiments, the variant of SEQ ID NO: 1 shares at least about 75%, 80%, 85%, 90%, 91%, 92%, 93%, 94%. 95%, 96%, 97%, 98%, or 99% identity with SEQ ID NO. 1. In certain embodiments, the plant IRES used in the constructs and methods provided herein has up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75 or 80 nucleotides substituted or deleted, while still able to permit translation of an internal RNA sequence operably linked to the IRES or to permit translation of an RNA sequence independently of a 5' cap. For example, the TriMV 5' UTR may require a stable structure such as that shown in FIG. 10, for function. Based on the predicted structure those of skill in the art will immediately envisage nucleotide substitutions that can maintain the structure of the TriMV 5' UTR and thus will likely also maintain the IRES function of the sequence. For example, any of the nucleotides shown to be in a base pairing relationship in the structure of FIG. 10 can be switched. In other words, the guanine at position 474 and the cytosine at position 481 may be switched to a cytosine at position 474 and a guanine at position 481. All similar substitutions on nucleotides based on the structure of FIG. 10 are included herein. These nucleotide substitutions are defined as variants of SEQ ID NO: 1. In some embodiments, the variants of SEQ ID NO: 1 retain the ability to initiate translation of a downstream coding sequence in a cap-independent manner and/or in the presence of an upstream stable hairpin structure. In other embodiments, the plant IRES of SEQ ID NO: 1 has 30, 40, 60, 80, 100, 125, 150, 175, 200, 225, 250, 275, 300, 325, 350, 375, 400, 425, 450, 475, or up to 500 nucleotides deleted and retains the ability to initiate translation of downstream coding sequences in a cap-independent manner and/or in the presence of a stable hairpin upstream of the IRES.

Also disclosed are fungi and plants, plant protoplasts and fungal, plant, bacterial and animal cells comprising the compositions described herein. The term "plant" includes reference to whole plants, plant organs (e.g., leaves, stems, roots, etc.), seeds, plant cells, and progeny of same. Parts of transgenic plants comprise, for example, plant cells, protoplasts, tissues, callus, embryos as well as flowers, ovules, stems, fruits, leaves, roots originating in transgenic plants or their progeny previously transformed with a DNA. As used herein, the term "plant cell" includes, without limitation, protoplasts and cells of seeds, suspension cultures, embryos, meristematic regions, callus tissue, leaves, roots, shoots, gametophytes, sporophytes, pollen, and microspores.

Plants include monocotyledonous and dicotyledonous plants. Plants include food crops, crop plants, fodder or forage legumes, ornamental plants, trees or shrubs. Examples of plants include, but are not limited to, chicory, carrot, cassava, trefoil, soybean, beet, sugar beet, sunflower, canola, alfalfa, rapeseed, linseed, cotton, tomato, potato and tobacco, sugarcane, rice, maize, wheat, barley, millet, rye, triticale, sorghum, emmer, spelt, einkorn, teff, milo, oats, cotton, oilseed rape including canola, sugarcane, *zoysia*, Sorghum, millet, Japanese millet, napier grass, switchgrass, *arabidopsis* and alfalfa.

Fungi include but are not limited to species of the genera *Fusarium, Aspergillus, Botrytus, Magnapothe, Puccinla, Blumeria, Mycosphaerella, Colletrotichum, Ustilago, Melampsora, Absidia, Acremonium, Alternarla, Candida, Saccharomyces, Phytophthora, Erysiphe, Cladosporium, Cryptococcus, Microsporum, Trichophyton, Epidermophyton, Sporotrix, Trichothecium, Trichophyton, Aureobasidium Stemphylium, Rhizopus, Phoma, Rhodotorula, Penicillium, Paecilomyces, Nigrospora, Mycogone, Neurospora, Mucor, Epicoccum, Helminthosporium, Gliocladium, Geotrichum, Epidermophyton, Drechslera, Cladosporium, Chaetomlum, Bipolaris*, or *Sclerotinia*.

Polypeptides which may be expressed using the compositions and methods disclosed herein include subunits of a multimeric protein, separate expression of each subunit of a polyprotein that need to go through proteolytic cleavage for activity such as insulin, multiple proteins from a multi-enzyme pathway, different proteins conferring different traits or which combine to produce a complex trait, expression of vaccines epitopes in plants, or expression of polypeptides capable of making a plant or cells useful as a nutraceutical or pharmaceutical.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are provided for illustrative purposes only and should not be construed as limiting.

EXAMPLES

Materials and Methods
Luciferase Reporter Constructs

A cDNA clone of the 5' UTR of TriMV (Wells, et al., (1998) *Mol Cell*, 2, 135-140) was used as a PCR template to generate the different clones. Restriction sites were added to PCR primers and used for cloning. The monocistronic TriMV firefly luciferase constructs were made in a T3 polymerase driven plasmid, c-myc-T3LUC(pA) (Thoma, et al., (2004) *Mol Cell*, 15, 925-935). The 5' UTR of TriMV, which spans from nt 1 to 739, and the derived mutants were amplified by PCR using a TriMV cDNA plasmid comprising 5'UTR sequence as a template. The PCR fragment was then digested with HindIII and NcoI restriction enzymes and ligated at the 5' end of the luciferase reporter gene into the HindIII and NcoI-cut cmyc-T3LUC (pA) plasmid. The cmyc-T3Luc (pA) plasmid contains a T3 RNA polymerase promoter followed by the c-myc untranslated region, which was removed by HindIII-NcoI digestion, and has a firefly luciferase reporter gene at its 3' end with 62 adenines downstream. Our control construct, which mimics a cellular mRNA, was derived from the pLGMS2 plasmid, which we obtained from Marvin Wickens' lab (University of Wisconsin-Madison) (Cooke, et al., (2010) *J Biol Chem*, 285, 28506-28513). It contains a firefly luciferase reporter gene flanked by 18 nt of vector sequence at its 5' end and a 39-nt poly(A) tail at its 3' end. It was linearized with BamHI to include the poly (A) tail or BgIII to exclude the poly(A) tail.

The TriMV, Turnip mosaic virus (TuMV), and the Tobacco etch virus (TEV) bicistronic constructs were derived from the pDluc plasmid, which was obtained from Allen Miller's lab (Iowa State University, Ames, Iowa). The pDluc plasmid contains a T7 RNA polymerase promoter, a renilla luciferase gene as the first open reading frame, an intergenic region with multiple cloning sites, a firefly luciferase gene as the second open reading frame, and a 60-nt long poly (A) tail. The PCR-generated TriMV 5' UTR and its derived mutants, and the TuMV and TEV 5' leaders were cloned into the intergenic region using XhoI and BgIII restriction enzymes. For the generation of the control construct (empty), following digestion with XhoI and BgIII, the sticky ends were treated with DNA Polymerase I Large fragment (Klenow) and religated to make an empty cassette.

For the insertion of the stable stem loop at the 5' end of pDluc to make SLpDluc, we synthesized and annealed two reverse complementary primers corresponding to the sequence of the stem loop: CGC GCG CAC GGC CCA AGC TGG GCC GTG CGC GCC (SEQ ID NO: 2) with NcoI sticky ends. The fragment was then inserted into the plasmid using the restriction site NcoI, immediately after the promoter. The reverse complementary sequences form a stable stem loop with a $\Delta G > -34$ kcal (Kozak, (1989) *Mol Cell Bioi*, 9, 5134-5142).

The TriMV and green fluorescent protein (GFP) free RNAs used in the trans-inhibition assay were in vitro transcribed using a PCR-based template. GFP free RNA was amplified from the TuMV infectious clone p35S::TuMV-GFP (Vijayapalani, et al., (2012) *PLoS Pathog*, 8, e1002639). Primers were designed to include the T7 RNA polymerase promoter at the 5' end, followed by the sequence of interest, TriMV 5' UTR or GFP. The resulting PCR products were used as templates for in vitro transcription. The 105 nt Barley yellow dwarf translation element (BTE) RNA was provided by Allen Miller's lab (Iowa State University) (Kraft, et al., (2011) *Acta Crystallogr Sect F Struct Biol Cryst Commun*, 67, 561-564).

Transcription

All RNAs were transcribed in vitro from linearized plasmids or PCR fragments using either the T7 MegaScript kit from Ambion or the T3 or T7 RNA polymerase from Fermentas. Monocistronic TriMV luciferase constructs were either linearized with SfcI to include the poly(A) tail or with SpeI to exclude the poly(A) tail. The pDluc derived constructs were linearized with BamHI to include the poly(A) tail. The control vector construct was linearized with BamHI to include the poly(A) tail or with BgIII to exclude the poly(A) tail. The renilla luciferase construct (Promega) was linearized with BamHI to include the poly(A) tail.

Reactions were assembled according to the transcription kit protocol. All mRNAs, unless specified, were synthesized in the presence of the 4-mM G (5') ppp (5') A cap analog (New England Biolabs). This ApppG cap analog increases the stability of the RNA without interfering with translation initiation and has no ability to recruit translation factors. For the synthesis of m7GpppG-capped mRNA, an mRNA with the methylated cap structure 4-mM 3'-0-Me-m7G (5') ppp (5') G (New England Biolabs) was added to the reaction. The in vitro transcription reaction was carried out for 2 hours at 37° C. Turbo DNase from the Ambion transcription kit was added to the reaction to degrade the template DNA before ethanol precipitation. Ethanol precipitation was performed by adding a 10% volume of 3M ammonium acetate followed by a 200% volume of absolute ethanol. The RNAs were then washed with 70% ethanol and resuspended in RNase free-water. RNA concentration was measured by a Nanodrop ND-1000 Spectrophotometer and RNA quality was verified on an agarose gel.

Translation Assay and Luciferase Read-out

The in vitro translation reactions were performed using the wheat germ extract system (Promega, Madison, Wis.). A 50 µl translation master mix was prepared with 0.1 pmol of RNA transcript, 25 µl wheat germ extract, 4 µl potassium acetate and 4 µl amino acid mix provided in the wheat germ extract kit (Guo, et al., (2000) *RNA*, 6, 1808-1820). RNAse-free water was used to bring the volume up to 50 µl. The master mix was then aliquoted for each replicate in a final volume of 10 µl. The reactions were assembled on ice. Each assay was performed in triplicate and repeated in at least three independent experiments. The RNA constructs were then translated at room temperature for 45 minutes. The reaction was stopped with the addition of 30 µl stop solution (Passive lysis buffer from the Promega Dual luciferase kit) to the 10 µl reaction. The luciferase activity of 10 µl of the resulting mixture was measured for 10 seconds on a Centro XS$^3$ LB 960 luminometer following injection of 10 µl of Luciferase Assay Reagent (Promega). For the dual luciferase assay, Stop&Glo reagent was added after the previous injection and measured for renilla luciferase activity for 6 seconds.

For the competition assays, the control m7GpppG-capped and polyadenylated vector mRNA construct was used for luciferase expression. Exogenous RNA or cap analog were added at the determined concentration to the translation reaction prior to the reporter mRNA. The in vitro translation reactions were performed as described above.

Translation Assay in Oat Protopasts

Oat protoplasts were prepared from cell suspension culture as described (Rakotondrafara, et al., (2007) *Current Protocols of Microbiology*, John Wiley & Sons, Inc., 16D.13.11-16D.13.12). 1 pmol of RNA reporter constructs were electroporated into 10$^6$ cells. For normalization, 0.1 pmol of capped polyadenylated renilla luciferase RNA construct was included in each electroporation. Four hours after electroporation, the cells were harvested, lysed in 500 µl passive lysis buffer (from the Promega Dual luciferase kit) and centrifuged for 10 min at 15,000 g. Next the luciferase activities were measured. 100 µl of the supernatant was added to 50 µl of the luciferase assay reagent II, and to which was added 50 µl of the stop-N-glo solution. All experiments were performed in triplicate and repeated in at least three independent experiments.

Protein Expression and Translation Assays

The wheat eIF4F, eIF4G and eIF4E recombinant proteins were prepared as described in Mayberry et al. ((2007) *Methods Enzymol*, 430, 397-408). In vitro translation assays with initiation factor proteins added in trans were performed in wheat germ extract in a total volume of 10 µl. In the trans-inhibition recovery assay, an increasing concentration of eIF4F, eIF4G or eIF4E from 0 to 100 nM was added.

Depleted extracts were prepared as described by Gallie and Browning (2001). A wheat germ extract (Promega) was loaded onto the m7GTP-sepharose affinity column (GE-Roche) equilibrated in 25 mM Hepes-KOH at pH 7.6, 100 mM KCl, 1 mM MgCl2 and 1 mM DTT. The unbound fraction was then collected and aliquoted for storage in −80 C prior to use.

Data Analysis

Each experiment was performed in triplicate and independently repeated at least three times. The translation measurements were plotted with the mean and the standard error of the mean (SEM) using GraphPad Prism 5. The translational value is expressed as relative luciferase activity (in percentage), fold-increase, or IRES activity, depending on the graph. For comparison of different monocistronic mRNA translation measurements, data was standardized by the mean of the control in each graph, which was set as 100% relative luciferase activity. To calculate fold-increase when comparing translation efficiency of RNA transcripts with or without a 5' m7GpppG cap, or that of RNAs with or without a 3' polyadenylated tail, means of luciferase measurements from constructs with no m7GpppG cap or no 3' poly (A) tail were set as 1-fold. The internal initiation activity was defined by the ratio of the firefly luciferase value over that of the renilla luciferase expressed on the bicistronic RNA.

For competition analysis with free RNA, data was standardized by the mean of the 0× exogenous RNA translation measurements, which were set as 100% relative luciferase activity. A two-tailed t-test was performed to show significant differences between measurements of different constructs with uneven variance.

Example 1

The TriMV 5' UTR Drives Efficient, Cap-independent Translation

The genomic RNA of *Triticum* mosaic wheat-infecting virus (TriMV) is naturally uncapped at its 5' end and polyadenylated at its 3' end (Seifers, et al. (2008) *Plant Disease*, 92, 808-817). To examine the function of the TriMV 5' leader in translation initiation, we engineered a firefly luciferase reporter construct flanked with the presumed TriMV 5' UTR (nt 1 to 739) at the 5' end and a 46 nt vector sequence at its 3' end followed by a 62-nt poly (A) tail (FIG. 1A). We then measured the translation efficiency of our TriMV reporter RNA in vitro in wheat germ extract in the presence of an ApppG cap at its 5' end. We compared this efficiency with that of a control luciferase RNA construct that contains vector sequences as 5' and 3' UTRs, a 7-methyl guanosine cap structure (m7GpppG) at its 5' end and a poly (A) tail at its 3' end. This construct mimics the structure of an eukaryotic messenger RNA. The ApppG cap analog stabilizes the mRNA, but unlike the m7GpppG cap, has no function in translation.

We first tested that the wheat germ extract reflected the cap and the poly(A) tail dependency of translation (Gallie. D. R. (1991) *Genes Dev*, 5, 2108-2116) (FIG. 1B, D). We measured the fold-increase of translation conferred by the m7GpppG cap analog on our polyadenylated control vector RNA, compared with that conferred by an ApppG cap analog. As expected, the m7GpppG cap boosted translation of the control RNA by 6-fold relative to that of the ApppG capped control RNA (FIG. 1B). We also compared the stimulation of translation conferred by the 3' poly(A) tail on an m7GpppG capped control RNA. In combination with the cap structure, the poly(A) tail stimulates translation by close to 5-fold compared with the capped non-adenylated mRNA (FIG. 1B). Together, these results support that the wheat germ in vitro system can recapitulate the cap- and poly(A) tail dependency of translation, and thus provides a reliable system to study the cap-mimicking function of the wheat-infecting TriMV 5' leader.

We then compared the translation efficiency of the TriMV reporter RNA construct with that of the control m7GpppG-capped polyadenylated control RNA (FIG. 1C). The result showed that the TriMV 5' UTR can drive cap-independent translation, with a translation output more than 1 fold greater than the control RNA. This cap-independence may be conferred by specific sequences or structures within the TriMV leader sequence. The reverse complement of the TriMV 5' UTR (TriMV reverse) failed to support translation of the reporter construct, when compared to the wild type TriMV sequence (FIG. 1C).

The presence of the m7GpppG cap on the TriMV reporter RNA boosted translation activity by less than 0.5-fold compared to the ApppG-capped mRNA (P-value: 0.005) (FIG. 1D), suggesting that the TriMV 5' UTR is sufficient to drive optimal translation in wheat germ extract. To examine the role of the poly(A) tail in TriMV-mediated translation, we measured the translation efficiency of the ApppG-capped TriMV mRNA construct with or without a 62-nt 3' polyadenylated tail (FIG. 1D). The 3' poly (A) tail provides about a 0.5-fold increase in translation (p value=0.001). Taken together, these results revealed that the TriMV 5' UTR supports efficient cap-independent translation at least in vitro that is modestly enhanced by a 3' poly (A) tail.

We further examined the ability of the TriMV 5' UTR to drive cap-independent translation in rabbit reticulocyte extract. Such extract has been extensively used to characterize polyviral translation elements (Carrington and Freed (1990) *J Virol*, 64, 1590-1597). We compared the translation efficiency of our ApppG-capped TriMV construct to that of the m7GpppG-capped control RNA as well as an ApppG-capped control RNA and the reverse complementary TriMV 5' UTR sequence RNA (FIG. 1E). Our data show that TriMV 5' UTR translated in rabbit reticulocyte lysate with poor efficiency as the ApppG-capped control RNA and the nonfunctional reverse complementary sequence TriMV reporter RNA, which are considered background level. Our data suggests that TriMV 5' UTR translation may be dependent upon plant and/or wheat specific host factors.

Example 2

The TriMV 5' UTR Drives Cap-independent Translation in vivo

To further characterize the translation activity of the TriMV 5' UTR, we measured the translation efficiency of the ApppG capped-TriMV firefly reporter RNA and the control capped polyadenylated RNA in oat protoplasts, a natural host of the virus (Tatineni, et al., (2009) *Phytopathology*, 99, 943-950) (FIG. 2). For internal control, we co-electroporated the RNA constructs with a capped polyadenylated renilla reporter RNA at 1:10 ratio. The results showed that the TriMV 5' UTR can drive cap-independent translation in vivo, with a translation output of the firefly luciferase gene more than 2 fold greater than the control capped polyadenylated RNA. This efficiency of translation was not linked to variations in manipulation and electroporation as shown with the renilla luciferase outputs.

To show that this strong efficiency of translation of the TriMV leader is not due to better RNA stability than the capped mRNA, we performed functional half-life RNA assays and did not find a significant difference in the half-lives of the RNAs.

Example 3

The TriMV 5' UTR Element Inhibits Cap-dependent Translation in Trans by Sequestering eIF4F The above observations prompted us to test whether the TriMV 5' UTR sequence is a functional RNA that can compete for binding of translation factors, and thus inhibit translation in trans (FIG. 3). We therefore measured the ability of the TriMV 5' UTR (nt 1 to 739) to interfere in trans with the translation of the capped polyadenylated control mRNA. We added to the in vitro translation reaction free RNA consisting only of the TriMV 5' UTR sequence (nt 1-739), up to a 20-fold molar excess over the m7GpppG-capped polyadenylated control mRNA. As a positive control, we used the well-characterized 105 nt Barley yellow dwarf virus cap-independent translation element (BTE), which supports efficient translation of uncapped mRNAs both in vivo and in vitro, and inhibits cap-dependent translation when added in trans. We used a 700-nt RNA sequence from the coding region of the green fluorescent protein (GFP) as a negative control. We measured the efficiency of trans-inhibition by the amount of exogenously added free RNA required to get 50% inhibition of cap-mediated translation. We set the translation level with no additional RNA (0-fold molar excess) as 100% relative luciferase activity. Our results revealed that free TriMV 5' UTR RNA interfered with cap-mediated translation in trans as efficiently as the BTE element (p value=0.05) (FIG. 3A). Similarly to the BTE, a 5-fold molar excess of the TriMV RNA decreased translation down to 50%. Even at high excess, the control GFP RNA showed little ability to inhibit translation, confirming the specificity of the assay.

BTE interacts specifically with the eIF4F complex in wheat germ extract and addition of eIF4F reverses the trans-inhibition of cap-dependent translation mediated by BTE. To determine whether eIF4F affects TriMV 5' UTR-mediated trans-inhibition, we added increasing concentrations of eIF4F (0 to 100 nM) to a translation reaction inhibited by a 20-fold molar excess of BTE or TriMV RNAs. And we measured recovery of translation. We set 100% relative luciferase as the level in the translation reaction of the capped polyadenylated mRNA with no trans-inhibitor. We found that similarly to the BTE (FIG. 3B), increasing concentration of eIF4F reversed the TriMV-mediated inhibition, with 100 nM sufficient to recover full translation (FIG. 3C). The scaffold component of the eIF4F complex, eIF4G, was also able to restore translation of the capped polyadenylated mRNA (FIG. 3D). However, the small cap-binding subunit, eIF4E, was unable to revert the loss of translation of the reporter mRNA caused by the TriMV 5' UTR (FIG. 3E). These results demonstrate that the TriMV 5' UTR sequence efficiently competes for binding for the eIF4F complex and at least for the large subunit eIF4G, but not for the eIF4E individual subunit. The data provide the first line of evidence that the TriMV 5' UTR can interact with the wheat cap binding complex, at least with eIF4G.

Example 4

TriMV 5' UTR-mediated Translation is Insensitive to Trans-inhibition by Cap Analog To further test the lack of dependency upon the cap binding factor eIF4E of TriMV-mediated translation, we measured the translation efficiency of the ApppG-capped TriMV reporter RNA in the presence of increasing concentrations of m7GTP cap analog (0-100 µM). Exogenous m7GTP cap analog normally inhibits cap-dependent translation by competitively sequestering eIF4E. We compared the level of translation of the TriMV reporter RNA to that of the control m7GpppG-capped polyadenylated RNA. As a negative control, we also tested increasing concentrations of non-competitive GTP. At 10 µM m7GTP, translation of capped control mRNA was reduced by 50% compared with GTP, and at 50 µM and above, translation was reduced to 30%. Conversely, addition of m7GTP cap analog had relative minor effect on TriMV-driven translation. The TriMV mRNA retained at least 75% of its translation at most given concentration of the inhibitor (p=0.01 for TriMV translation and p=0.002 for control mRNA translation at 80-µm GTP versus 80 µm m7GTP, FIG. 4). We conclude that TriMV-mediated translation is largely unaffected under eIF4E-limiting condition that impairs cap-dependent translation.

Example 5

The TriMV Translation is eIF4F-dependent

Having determined the ability of the TriMV UTR to compete for eIF4F, we next analyzed the dependence upon this complex for translation. We made the wheat germ extract dependent on cap-binding complex (eIF4F/eIFiso4F) by passing through a m7GTP-sepharose column. This process was previously shown to deplete the cap-binding complex, including eIF4E and eIF4G, their isoforms eIFiso4E and eIFiso4G, and along with some eIF4A, eIF4B and PABP. We next measured translation efficiency via the percentage of incorporation of the $^{35}$S-labelled leucine amino acid in the newly synthesized protein, in the presence of increasing concentration of eIF4F (0-10 pmol), or each of its subunits, eIF4G and eIF4E individually. TriMV translation was fully dependent on exogenously added translation factors (FIG. 5). Maximal translation was reached with the addition of eIF4F. eIF4E alone did not stimulate translation, whereas the addition of the large subunit eIF4G was sufficient to support translation. Taken together, the TriMV-mediated translation is supported by eIF4F, but it is clearly eIF4E-independent.

Example 6

Translation Initiates at the AUG at Position nt 740

Figure 6:
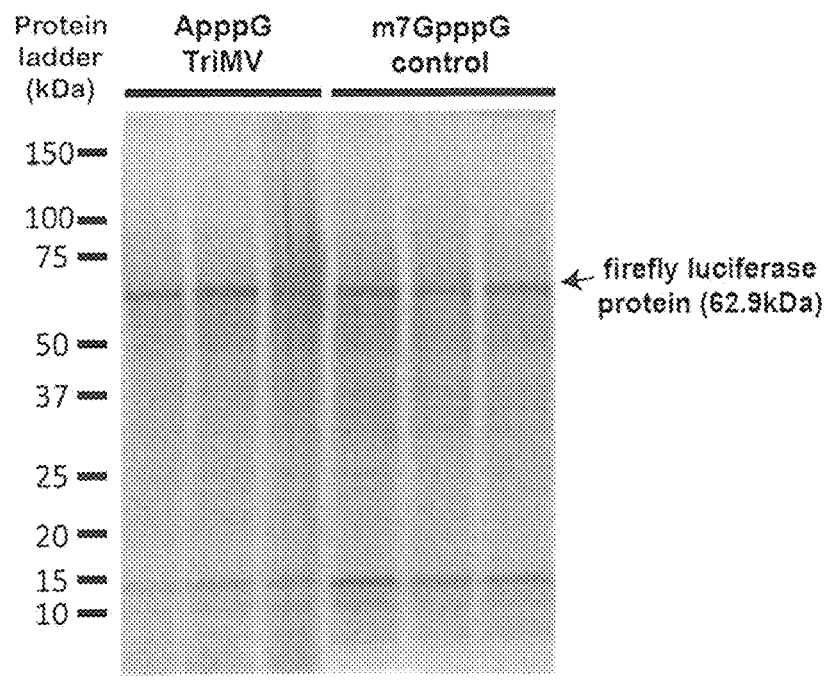
FIG. 6 is a photograph of a radiograph showing that the luciferase expressed by the expression constructs have the correct predicted size and are using the AUG at position 740 of the TriMV 5' UTR (SEQ ID NO: 1).

The TriMV 5' leader sequence contains 12 AUGs upstream of the presumed start codon at position nt 740. Our sequence analysis reveals that four of these AUGs (bps 116-118, 146-148, 281-283 and 333-335) are in frame with the presumed correct initiation site. The AUGs at positions 116-118 nt. 333-335 nt, 501-503 nt, 561-563 nt and 598-600 nt are in a good context (G at position +4 and A/C at position −2). The AUGs at position nt 281-283, 525-527 and 598-561 could potentially encode for uORFs of about 33, 64, 77 amino acids, respectively. To verify the authenticity of the AUG at position nt 740, which corresponds to the AUG of the luciferase gene in our TriMV construct as the correct initiation site, we performed an in vitro translation assay in the presence of $^{35}$S-labelled methionine and ran the reaction on a 4-15% SDS page gel (FIG. 6). We observed the accumulation of the firefly luciferase protein at the expected molecular size (62.9 kDA). The assay revealed that the protein expression pattern of the TriMV RNA was identical to that of our control capped polydadenylated mRNA. Our data suggest that the AUG at position nt 740 is the correct AUG and the upstream AUGs in the TriMV leader sequence may not be utilized in translation. This is in line with a non-canonical mechanism of translation that may not involve scanning from the 5' end of the mRNA nor recognition of the 5' proximal AUGs.

Example 7

The 5' UTR of TriMV can Drive Internal Translation

The above results suggest that the translation of the TriMV element may not be dependent upon a 5' cap, the cap binding factor eIF4E, or possibly scanning from the 5' end to reach the correct initiation site. These results prompted us to assess whether the TriMV 5' UTR can mediate translation from an internal position in a 5' end-independent manner. We inserted the TriMV 5' UTR between a renilla luciferase and a firefly luciferase reporter gene in a standard bicistronic RNA (FIG. 7A). The expression of the downstream, second cistron (firefly luciferase) depends on the internal initiation activity of the element placed in the intergenic region. We tested the bicistronic polyadenylated mRNA in wheat germ extract with an ApppG or an m7GpppG cap analog at its 5' end. We measured the ratio of firefly luciferase activity to renilla luciferase activity. We compared the translational activity of the TriMV leader sequence to the TEV and TuMV 5' UTRs, which are reported to act as IRESes, and to no insertion (empty control). The TriMV 5' UTR directed internal initiation, in the context of ApppG or m7GpppG-capped RNA, well above the baseline level of empty control and with better efficiency than the TEV and TuMV 5'UTRs (FIG. 7A).

To carefully exclude the possibility that the translation of the downstream firefly luciferase depends on the translation of the first cistron, we introduced a stable hairpin (ΔG=−34 kcal) immediately after the 5' end of the mRNAs to block ribosomal scanning. This strong hairpin impairs translation of the first cistron, and leaves translation of the downstream cistron strictly dependent on internal initiation. We compared the TriMV activity to that of the controls (TEV and TuMV 5' UTRs, and the empty control) in ApppG- and m7GpppG-capped RNA constructs (FIG. 7B). Our results showed that the stable hairpin at the 5' end of the mRNA had no effect on the ability of the TriMV 5' UTR to drive translation. The TriMV 5' UTR sustained strong translation of the downstream ORF, far above the empty control and the TEV and TuMV 5' UTRs, which were at background level (FIG. 7B). Our results thus show unlike TEV and TuMV elements, internal initiation from the TriMV 5' leader is clearly 5' end-independent. It is worth noting that the relative values are higher in the bicistronic constructs with the stable stem loop as the hairpin fully inhibited cap-dependent translation, resulting in a baseline level of the renilla luciferase activity over that of the firefly luciferase. Differential values of IRES activity are also observed with the ApppG vs m7GpppG capped constructs in FIG. 7A due to the baseline translation of ApppG capped mRNA.

Example 8

A 300 nt Region is Sufficient for Cap-independent Translation

To establish the region within the TriMV leader that is responsible for conferring cap-independent translation, we roughly truncated the 739 nt TriMV 5' UTR from its 5' and 3' ends and tested the translation efficiency of the mutant derivatives in the monocistronic reporter construct with an ApppG cap at its 5' end (FIG. 8A). We compared the translation output of the mutants to the full-length TriMV 5' UTR. As shown in FIG. 7B, a deletion of the first 401 nt from the 5' end had little effect on the ability of the TriMV to drive cap-independent translation. Mutant 442-739, which has a deletion of the nucleotides 1-441, showed an increase in translation of the luciferase reporter than the full-length TriMV 5' UTR (p value=0.01). However, further 5' deletion (mutants 539-739 and 549-739) caused significant reduction in translation (FIG. 8B).

To rule out the possibility that a loss of RNA stability caused the loss of translation observed with 5' deletion mutants, we estimated the functional half-lives of the full-length TriMV (1-739) and the mutant RNAs (442-739 and 539-739) by monitoring the rate of luciferase accumulation in wheat germ extract over a 3 hour time course (Table 1). We defined the functional half-life of the mRNA as the time to reach the half-maximum accumulation of luciferase expression, minus the lag time. We used GraphPad software to generate the best-fitting curves to the experimental data. Our analysis revealed that the mutant RNAs had similar functional half-lives to the wild type TriMV construct, which showed a half-life of 57.19 minutes. Interestingly, the mutant 442-739 had a half-life of 78.86 minutes, consistent with its increased translation efficiency (FIG. 8B). We concluded that the observed loss of translation efficiency of RNA constructs with deletions (FIG. 8B) results from regulation at the translation level, not RNA instability.

TABLE 1

RNA functional half-life of mutants. The functional half-life of the mRNA was determined as the time to reach the half-maximum accumulation of luciferase expression, minus the lag time. The best fitting curves to the experimental data points were generated using GraphPad software.

| | mutant construct (nt) | | | | |
|---|---|---|---|---|---|
| | 1-739 | 1-601 | 442-739 | 490-739 | 442-709 |
| Half life (minutes) | 57.19 | 66.09 | 78.86 | 63.61 | 53.28 |
| $R^2$ | 0.8674 | 0.9892 | 0.9272 | 0.9855 | 0.8856 |

To further test the functionality of the 5' deletions, we performed an in vitro trans-inhibition assay and compared the efficiency of inhibition of cap-dependent translation in trans of the free mutant RNAs (nts 442-739 and 539-739) to the full length TriMV UTR (nts 1-739), to control BTE and to the unrelated, non-functional RNA (GFP). The results from the in vitro trans-inhibition assays corroborate our in cis luciferase data (FIG. 8C). A 10-fold molar excess of nts 442-739 free RNA decreased translation by 80%, suggesting that it actively competes for the factors required for cap-dependent translation. However, the presence of a 20-fold molar excess of nts 539-739 free RNA had no effect on translation, similar to the non-functional control GFP RNA. The inability of mutant 539-739 free RNA to inhibit translation in trans is consistent with its inability to drive translation in cis (FIG. 8B). These observations suggest that the 5' region of TriMV leader necessary for cap-independent translation and factor binding resides between nt 442 and 739.

We also made deletions from the 3' end of the TriMV 5' UTR (FIG. 8A). We tested each deletion mutant in a monocistronic reporter and as free RNA in the in vitro trans-inhibition assay. A deletion of 30 nt from the 3' end (mutant 1-709) conferred full translation of the mRNA. However, further truncation (mutant 1-601 and 1-550) abolished translation (FIG. 8D). RNAs of mutants 1-550 and 1-601 have similar functional half-lives as the full length 1-739 TriMV construct (FIG. 8G). Therefore, the loss of translation does not occur with a loss of RNA stability. Next, we performed the in vitro trans-inhibition assay of capped RNA with a molar excess of the mutant free RNAs (1-709, 1-550, or 442-739), and control BTE and GFP RNAs. Despite its inability to mediate translation in cis, the 1-550 truncated RNA does inhibit translation of capped and poly-adenylated mRNA in trans as efficiently as 1-709 and 442-739 free RNAs (FIG. 8E). Next we examined the ability of the deletion mutant 442-709 to drive cap-independent translation, compared with the full length TriMV 5' UTR RNA. Our results show that the 442-709 RNA construct supported translation of about 50% compared to the full-length 5' UTR RNA (FIG. 8F). While functional, the mutant showed a weaker trans-inhibition activity. This sequence requirement analysis suggests that while region 442-709 retains 50% of translational activity of the full length UTR, regions 442-739 and 1-709 within the TriMV 5' leader sequence confer optimal cap-independent translation, at least in vitro.

To corroborate the ability of mutant RNAs to drive cap-independent translation from a 5' end position with internal initiation activity, we measured the translational activity of our mutant sequences (442-739 and 1-709) in the context of the intergenic region of an m7GpppG bicistronic RNA and compared their activities to that of full-length leader sequence (nts 1-739) (FIG. 8G). Our results revealed that the region 442 to 739 is unable to drive translation from an internal position. However, the 1-709 nt sequence supported 50% of the translation level of the full length TriMV 5' UTR sequence. To identify the additional sequences required for optimal IRES activity, we tested regions 300-739 and 100-739. The nt 300-739 construct had no activity, but the 100-739 construct supported translation at half activity of the full length 5' UTR sequence (FIG. 8G). Taken together, our results indicate that the minimal sequences sufficient to drive cap-independent translation from a 5' leader position are not sufficient to drive maximal translation from an internal position. The later requires the entire 739 nt 5' UTR for optimal activity.

Example 9

The TriMV 5' UTR has IRES Activity in Plants

We will also test the ability of the TriMV IRES activity using the monocistronic and bicistronic constructs in tobacco plants in a transient expression assay through *agrobacterium* Infiltration. We expect the TriMV 5' UTR will have IRES activity to drive expression of both monocistronic and bicistronic constructs as already demonstrated in vitro.

What is claimed is:

1. A construct comprising an internal ribosome entry site (IRES) sequence consisting of a *Triticum* mosaic virus (TriMV) segment consisting of nucleotides 442-739 of SEQ ID NO: 1 or a TriMV segment consisting of nucleotides 1-709 of SEQ ID NO: 1, wherein said IRES is operably linked to heterologous sequences at both the 5' end and the 3' end, and wherein the 3' end is operably connected to a first heterologous coding sequence encoding a first polypeptide, wherein under appropriate conditions the construct mediates translation of the first heterologous coding sequence and production of the first polypeptide.

2. The construct of claim 1, wherein the start codon of the first coding sequence immediately follows the IRES.

3. The construct of claim 1, wherein the construct is DNA.

4. The construct of claim 1, further comprising a promoter operably linked to the IRES.

5. A vector comprising the construct of claim 1.

6. A cell comprising the construct of claim 1.

7. The cell of claim 6, wherein the cell is a plant cell.

8. A transgenic plant comprising the construct of claim 1.

9. The construct of claim 4, wherein a second heterologous coding sequence is operably linked between the promoter and the IRES.

10. A method for expressing at least two heterologous polypeptides in a plant cell, said method comprising introducing the construct of claim 9 into the plant cell.

11. The method of claim 10, further comprising expressing a third polypeptide in the cell, wherein the construct comprises a second IRES segment consisting of nucleotides 442-709 of SEQ ID NO: 1 downstream of the first and second coding sequence and operably linked to a third coding sequence encoding the third polypeptide.

12. The method of claim 10, wherein the first polypeptide and second polypeptide are different units of a multimeric protein, or confer two different traits, or are part of a multi-enzymatic pathway.

13. The method of claim 12, wherein the method is used to make a pharmaceutical or biologic molecule.

14. A method for expressing a polypeptide in a cell-free translation system, the method comprising contacting the construct of claim 1 with a cell-free translation system from wheat germ, whereby the polypeptide is expressed.

15. The method of claim 14, wherein the construct further comprises a second coding sequence encoding a second polypeptide upstream of the IRES, and wherein the first polypeptide and the second polypeptide are translated.

* * * * *

SEQUENCE LISTING

```
<160> NUMBER OF SEQ ID NOS: 2

<210> SEQ ID NO 1
<211> LENGTH: 742
<212> TYPE: DNA
<213> ORGANISM: triticum mosaic virus

<400> SEQUENCE: 1
aaaattaaag atcatattac ataaaataac ataatataaa atcacttaaa atcatgtgtt     60
ttaaactacg cttagtttaa ttagttttgg tgcgtttagc gattcgtcat tgtacatggt    120
gtgttgtgtg ttttatgatt ttagtatgtt tcttaaatta ttgaagccct ataaggaccg    180
gctataaacg tcctgttttc aagtgggaaa agaaaccact cgccttacca ctagctggga    240
tctagctaga gctccggcgt aaaacgagct acgcttttgg atgcagcgtt acgcattcct    300
gggcttaggc gattgtacta caatgggtag cccccagtgc cagtttttgg cccgctattg    360
tattacaatt cggttaagtt aacttggttg gaaacaagcc aaatgctagc tatcattcgc    420
attcggacat gaggaaggtg aacgcagtga atcatagtgg tggtacgctc ttggggtggt    480
tcccaagact tcgtagggct atggttagct gttagtaaga cctaatgttc gtttgtgata    540
cagtcgaaag ttgtttccgt atggagctcg gtctgcgcgt taagcaccag cctgactatg    600
ggcagtatcc ctgtttttcc actattctca ctatcaacca caacgcacga ctttctgctc    660
tcttggcact ttcttacttt cacactctcg cgctcgtttc aaagttttat tacttctctt    720
tttctcctga ccattcacga tg                                              742

<210> SEQ ID NO 2
<211> LENGTH: 33
<212> TYPE: DNA
<213> ORGANISM: artificial
<220> FEATURE:
<223> OTHER INFORMATION: synthetic

<400> SEQUENCE: 2
cgcgcgcacg gcccaagctg ggccgtgcgc gcc                                  33
```